(12) United States Patent
Yamazaki et al.

(10) Patent No.: US 8,581,970 B2
(45) Date of Patent: Nov. 12, 2013

(54) LIVING BODY OBSERVATION DEVICE

(75) Inventors: Kenji Yamazaki, Hino (JP); Kazuhiro Gono, Sagamihara (JP); Takeshi Urasaki, Tachikawa (JP); Takashi Takemura, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1118 days.

(21) Appl. No.: 12/210,672

(22) Filed: Sep. 15, 2008

(65) Prior Publication Data

US 2009/0040298 A1 Feb. 12, 2009

Related U.S. Application Data

(63) Continuation of application No. PCT/JP2007/053088, filed on Feb. 20, 2007.

(30) Foreign Application Priority Data

Mar. 16, 2006 (JP) ................................. 2006-073183

(51) Int. Cl.
*A61B 1/06* (2006.01)
(52) U.S. Cl.
USPC .......................................................... 348/65
(58) Field of Classification Search
USPC .......... 348/65, 66–76, 45; 600/101, 109, 160, 600/178, 180–181
See application file for complete search history.

(56) References Cited

U.S. PATENT DOCUMENTS

| 2003/0158470 | A1  | 8/2003  | Wolters et al. |
| 2003/0176768 | A1* | 9/2003  | Gono et al. ................... 600/109 |
| 2004/0225185 | A1* | 11/2004 | Obata et al. ................... 600/118 |
| 2005/0096505 | A1* | 5/2005  | Imaizumi et al. ............. 600/180 |

FOREIGN PATENT DOCUMENTS

| EP | 1 302 152 A1 | 4/2003 |
| EP | 1 527 729 A1 | 5/2005 |
| GB | 2 068 537 A  | 8/1981 |
| JP | 2002-095635  | 4/2002 |
| JP | 2003-093336  | 4/2003 |
| JP | 2005-131130  | 5/2005 |
| JP | 2005-185541  | 7/2005 |
| JP | 2005-198750  | 7/2005 |
| JP | 2005-296200  | 10/2005 |
| WO | WO 02/07588 A1 | 1/2002 |

OTHER PUBLICATIONS

Extended Supplementary European Search Report dated Mar. 29, 2010.

* cited by examiner

*Primary Examiner* — Ruolei Zong
(74) *Attorney, Agent, or Firm* — Scully, Scott, Murphy & Presser, P.C.

(57) ABSTRACT

A light source unit, which is connected to a control unit and an endoscope, radiates a pre-determined light quantity of white light based on a signal from the control unit. The light source unit includes a lamp as a white light source, an infrared cut filter, a light quantity limiting filter, being inserted/removed on an optical path, for limiting light quantity in a pre-determined wavelength region of white light, a filter insertion/removal driving unit for inserting/removing the light quantity limiting filter on an optical path, and a condensing lens for outputting white light. For example, when a transmission rate of a blue band is 100%, the light quantity limiting filter limits transmission rates of other bands to 50%. This improves S/N in discrete spectral image generation with illumination light in a visible light region.

4 Claims, 20 Drawing Sheets

FIG.3
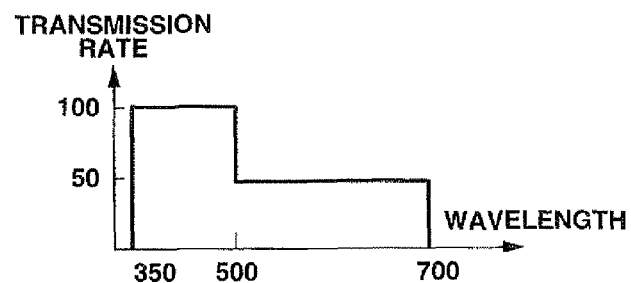
FIG.4
| R | G | R | G |
|---|---|---|---|
| R | B | R | B |
| R | G | R | G |
| R | B | R | B |
FIG.5
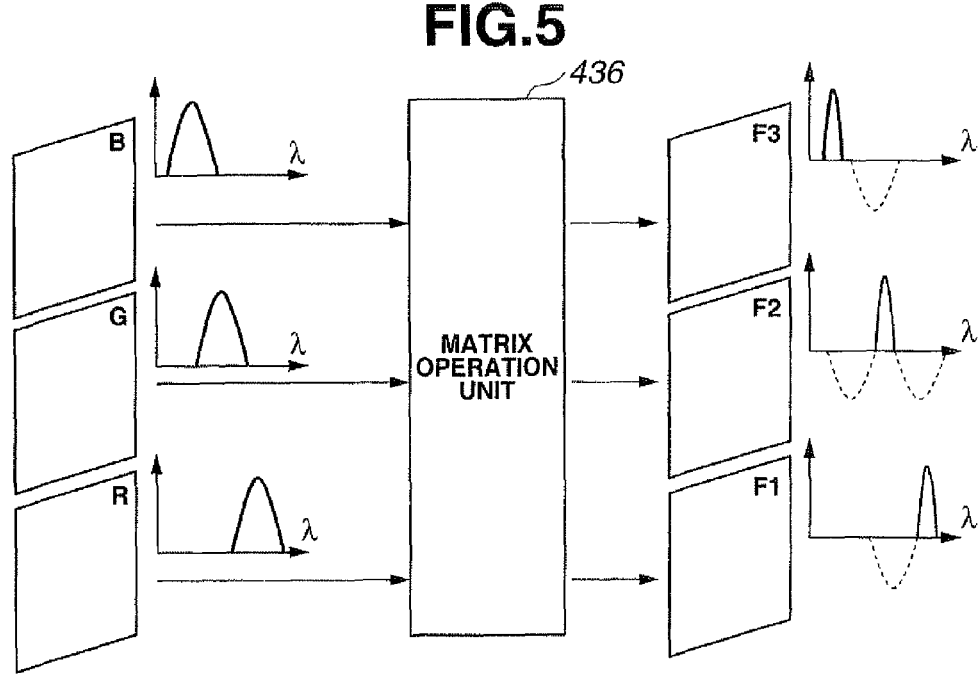

| | λ1 | λ2 | λ3 |
|---|---|---|---|
| SET 1 | 400nm | 445nm | 500nm |
| SET 2 | 425nm | 500nm | 600nm |
| SET 3 | 450nm | 540nm | 650nm |
| SET 4 | 475nm | 570nm | 700nm |

SET WAVELENGTH SET OF SPECTRAL IMAGE (208)

FIG.19

SET WAVELENGTH SET OF SPECTRAL IMAGE

|  | λ1 | λ2 | λ3 |
|---|---|---|---|
| SET 1 | 400nm | 445nm | 500nm |
| SET 2 | 425nm | 500nm | 600nm |
| SET 3 | 450nm | 540nm | 650nm |
| SET 4 | 475nm | 570nm | 700nm |

SELECT

FIG.20

SET WAVELENGTH SET OF SPECTRAL IMAGE

|  | λ1 | λ2 | λ3 |
|---|---|---|---|
| SET 1 | 400nm | 445nm | 500nm |
| SET 2 | 425nm | 500nm | 600nm |
| SET 3 | 450nm | 540nm | 650nm |
| SET 4 | 475nm | 570nm | 700nm |

SELECT

LIVING BODY OBSERVATION DEVICE

CROSS REFERENCE TO RELATED APPLICATION

This application is a continuation application of PCT/JP2007/053088 filed on Feb. 20, 2007 and claims benefit of Japanese Application No. 2006-073183 filed in Japan on Mar. 16, 2006, the entire contents of which are incorporated herein by this reference.

BACKGROUND OF THE INVENTION

1. Field of the Invention

The present invention relates to a living body observation device for using a color image signal obtained by picking up an image of a living body to display the image as a spectral image on a display device by signal processing.

2. Description of the Related Art

Conventionally, an endoscope device for obtaining an endoscope image in a body cavity by radiating illumination light is widely used as a living body observation device. This kind of endoscope device uses an electronic endoscope including an image pickup unit for guiding illumination light from a light source into a body cavity using a light guide and picking up an image of a shooting object by optical feedback of the light. Such device processes an image pickup signal from the image pickup unit by a video processor to display an endoscope image on an observation monitor and observe an observed part such as a diseased part.

As one scheme in performing normal observation of living tissue by an endoscope device, a light source emits white light in a visible light region, and irradiates an shooting object with frame sequential light via an RGB rotating filter, for example, and a video processor synchronizes optical feedback of the frame sequential light and processes an image to obtain a color image. As another scheme in performing normal observation of living tissue by the endoscope device, color chips are arranged on a front surface of an image pickup surface of the image pickup unit of the endoscope, the light source emits white light in a visible light region and the color chips separate optical feedback of the white light into respective color components to pick up an image, and the video processor processes an image to obtain a color image.

Living tissue has different light absorption characteristics and scattering characteristics depending on wavelengths of radiated light. As such, Japanese Patent Application Laid-Open Publication No. 2002-95635, for example, discloses a narrowband-light endoscope device for irradiating living tissue with illumination light in a visible light region as narrowband RGB frame sequential light with discrete spectral characteristics and obtaining tissue information of a desired deep part of the living tissue.

Japanese Patent Application Laid-Open Publication No. 2003-93336 discloses a narrowband-light endoscope device for processing an image signal with illumination light in a visible light region, generating a discrete spectral image, and obtaining tissue information of a desired deep part of living tissue.

In the device according to Japanese Patent Application Laid-Open Publication No. 2003-93336, a light quantity control unit performs processing to decrease illumination light quantity to obtain a spectral image (for example, illumination light radiation timing control, light chopper control, lamp application current control or electronic shutter control) for the illumination light quantity to obtain a normal light observation image, and controls to avoid saturation of a CCD being an image pickup unit.

SUMMARY OF THE INVENTION

A living body observation device according to one aspect of the present invention is a living body observation device comprising a signal processing control unit for controlling operation of an illumination source for irradiating a living body being a subject with light and/or an image pickup unit for photoelectrically converting light reflected from the living body based on the illumination light from the illumination source and for generating an image pickup signal, and for outputting the image pickup signal to a display device, the living body observation device including:

a spectral signal generation unit for generating a spectral signal corresponding to a band image of a discrete spectral distribution of said subject from the image pickup signal by signal processing; and a color adjustment unit for adjusting a color tone for each of a plurality of bands forming the spectral signal when the spectral signal is outputted to the display device, wherein a spectral characteristics control unit for controlling spectral characteristics of light on an optical path is further provided on the optical path from the illumination source to the image pickup unit.

BRIEF DESCRIPTION OF THE DRAWINGS

FIG. 3 is a diagram showing transmission characteristics of a light quantity limiting filter in FIG. 2;

FIG. 4 is a diagram showing arrangement of color filters provided on a front surface of a CCD in FIG. 2;

FIG. 5 is a diagram illustrating a matrix calculation method of calculating a matrix in a matrix operation unit in FIG. 2;

FIG. 19 is a fourth diagram illustrating the graphic user interface with the function of the touch-sensitive panel in FIG. 2;

FIG. 20 is a fifth diagram illustrating the graphic user interface with the function of the touch-sensitive panel in FIG. 2;

DESCRIPTION OF THE PREFERRED EMBODIMENT(S)

The following will describe embodiments of the present invention with reference to the drawings.

(First Embodiment)

Figure 1:
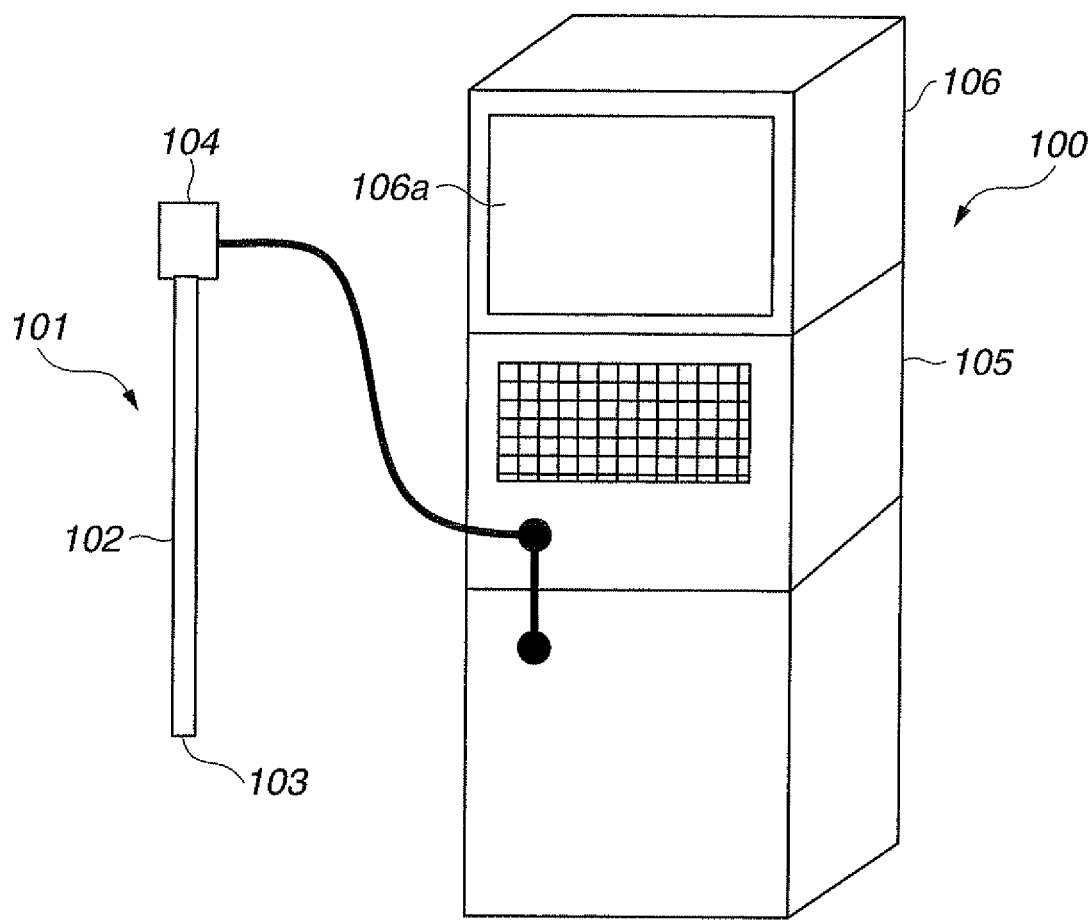
FIG. 1 is an outline view showing an appearance of an electronic endoscope device according to a first embodiment of the present invention.
Figure 2:
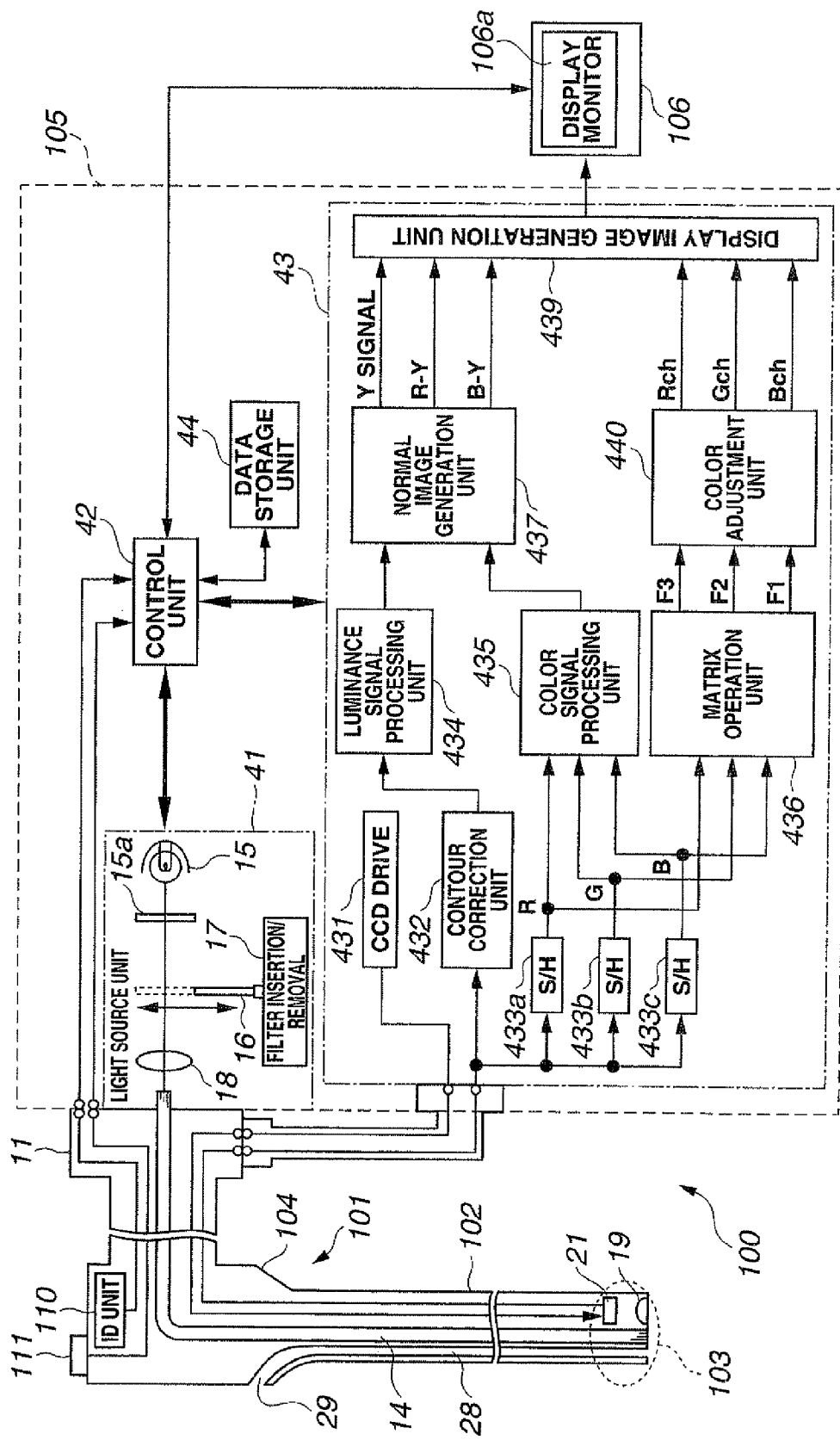
FIG. 2 is a block diagram showing configuration of the electronic endoscope device in FIG. 1.
Figure 6:
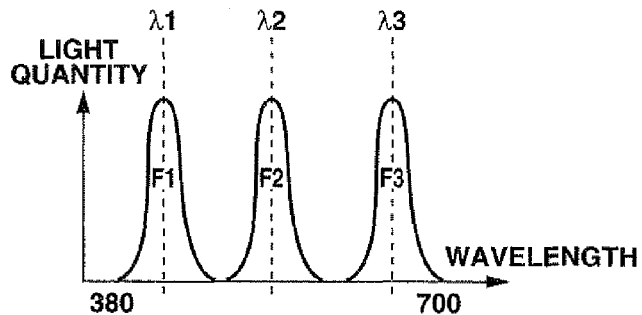
FIG. 6 is a diagram showing spectral characteristics of spectral images generated by the matrix operation unit in FIG. 2.
Figure 7:
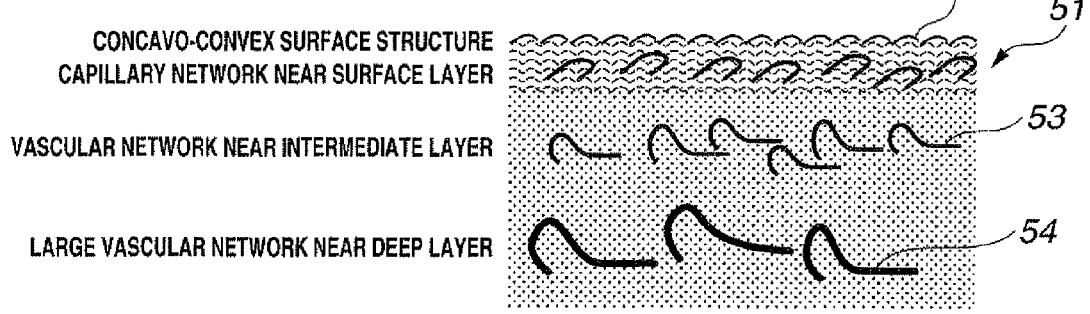
FIG. 7 is a diagram showing a structure in a layer direction of living tissue observed by an electronic endoscope device in FIG. 2.
Figure 8:
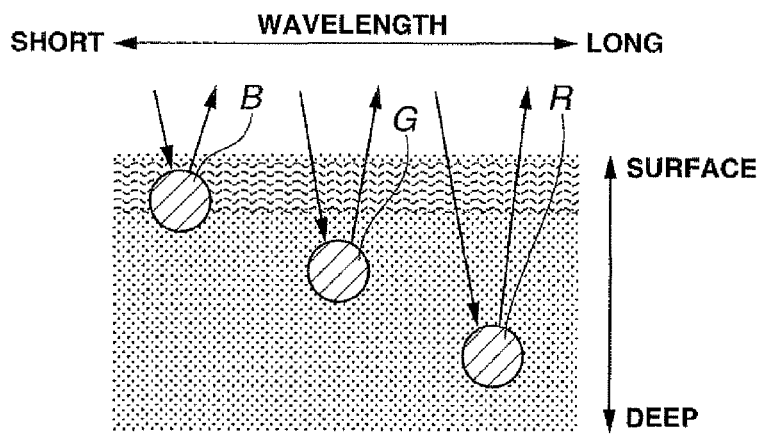
FIG. 8 is a diagram illustrating a state of illumination light from the electronic endoscope device in FIG. 2 reaching living tissue in the layer direction.
Figure 9:
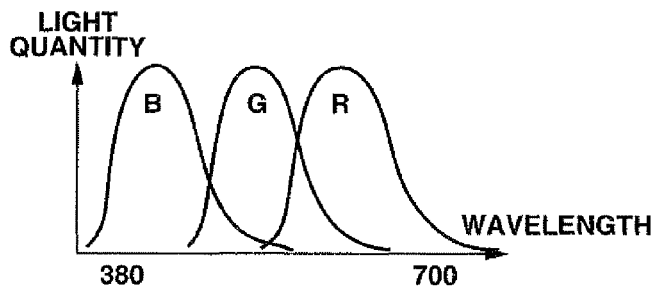
FIG. 9 is a diagram showing spectral characteristics of each band of RGB light during normal observation by the electronic endoscope device in FIG. 2.
Figure 10:
FIG. 10 is a first diagram showing a band image with RGB light during the normal observation in FIG. 9.

FIGS. 1 to 36 relate to a first embodiment of the present invention. FIG. 1 is an outline view showing an appearance of an electronic endoscope device; FIG. 2 is a block diagram showing configuration of the electronic endoscope device in FIG. 1; FIG. 3 is a diagram showing transmission characteristics of a light quantity limiting filter in FIG. 2; FIG. 4 is a diagram showing arrangement of color filters provided on a front surface of a CCD in FIG. 2; FIG. 5 is a diagram illustrating a matrix calculation method of calculating a matrix in a matrix operation unit in FIG. 2; FIG. 6 is a diagram showing spectral characteristics of spectral images generated by the matrix operation unit in FIG. 2; FIG. 7 is a diagram showing a structure in a layer direction of living tissue observed by an electronic endoscope device in FIG. 2; FIG. 8 is a diagram illustrating a state of illumination light from the electronic endoscope device in FIG. 2 reaching living tissue in the layer direction; FIG. 9 is a diagram showing spectral characteristics of each band of RGB light during normal observation by the electronic endoscope device in FIG. 2; and FIG. 10 is a first diagram showing a band image with RGB light during the normal observation in FIG. 9.

Figure 11:
FIG. 11 is a second diagram showing a band image with RGB light during the normal observation in FIG. 9.
Figure 12:
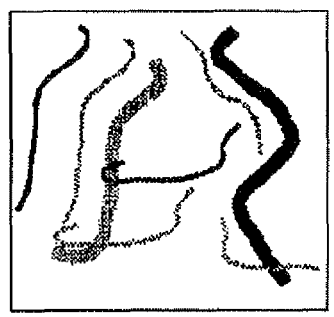
FIG. 12 is a third diagram showing a band image with RGB light during the normal observation in FIG. 9.
Figure 13:
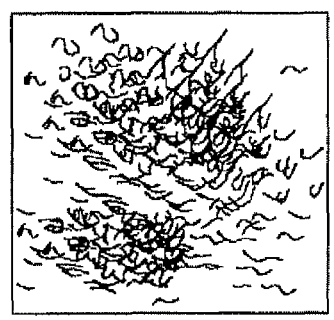
FIG. 13 is a first diagram showing one of the spectral images in FIG. 6.
Figure 14:
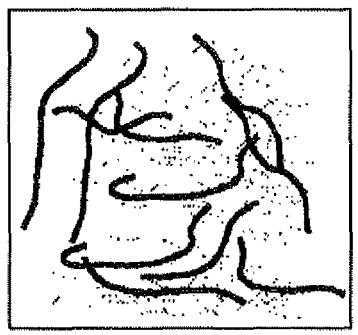
FIG. 14 is a second diagram showing one of the spectral images in FIG. 6.
Figure 15:
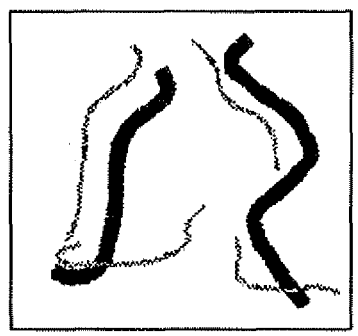
FIG. 15 is a third diagram showing one of the spectral images in FIG. 6.
Figure 16:
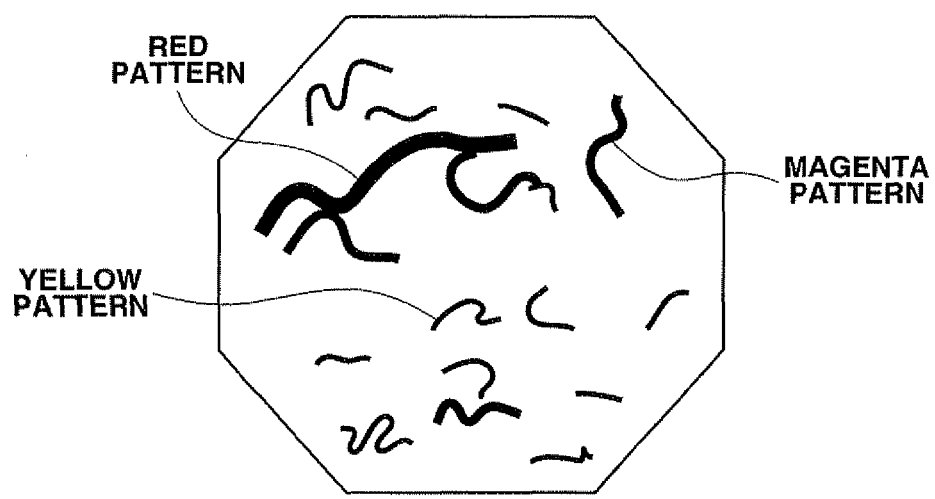
FIG. 16 is a first diagram illustrating a graphic user interface with a function of a touch-sensitive panel in FIG. 2.
Figures 17, 18:
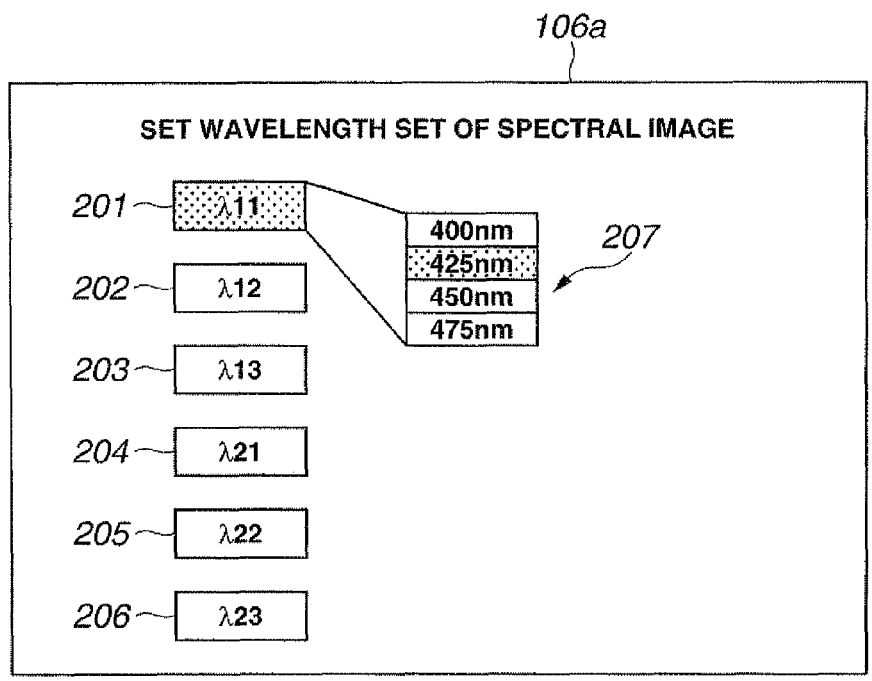
FIG. 17 is a second diagram illustrating the graphic user interface with the function of the touch-sensitive panel in FIG. 2.
FIG. 18 is a third diagram illustrating the graphic user interface with the function of the touch-sensitive panel in FIG. 2.

FIG. 11 is a second diagram showing a band image with RGB light during the normal observation in FIG. 9; FIG. 12 is a third diagram showing a band image with RGB light during the normal observation in FIG. 9; FIG. 13 is a first diagram showing one of the spectral images in FIG. 6; FIG. 14 is a second diagram showing one of the spectral images in FIG. 6; FIG. 15 is a third diagram showing one of the spectral images in FIG. 6; FIG. 16 is a first diagram illustrating a graphic user interface with a function of a touch-sensitive panel in FIG. 2; FIG. 17 is a second diagram illustrating the graphic user interface with the function of the touch-sensitive panel in FIG. 2; FIG. 18 is a third diagram illustrating the graphic user interface with the function of the touch-sensitive panel in FIG. 2; FIG. 19 is a fourth diagram illustrating the graphic user interface with the function of the touch-sensitive panel in FIG. 2; and FIG. 20 is a fifth diagram illustrating the graphic user interface with the function of the touch-sensitive panel in FIG. 2.

Figure 21:
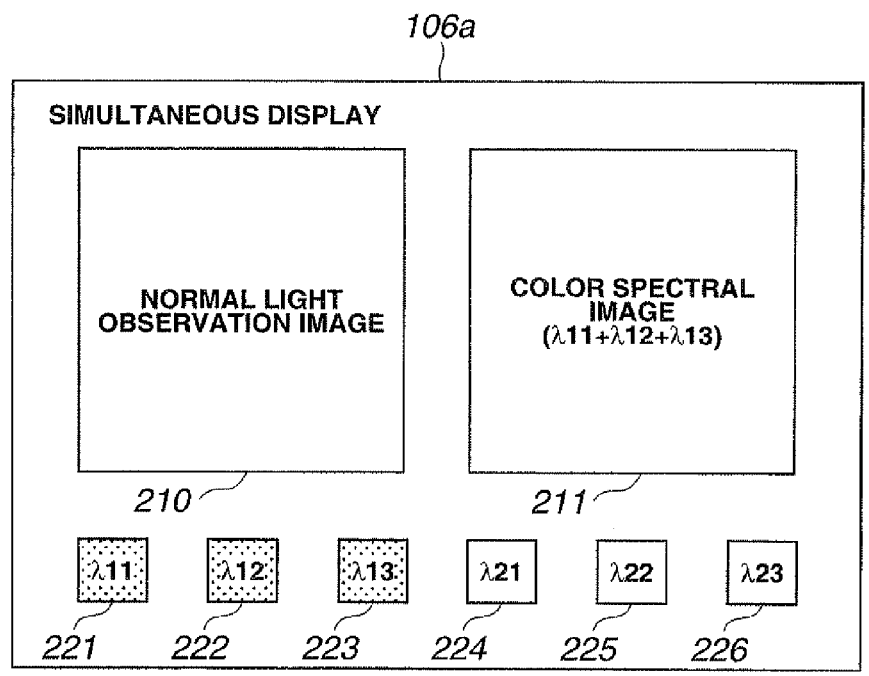
FIG. 21 is a sixth diagram illustrating the graphic user interface with the function of the touch-sensitive panel in FIG. 2.
Figure 22:
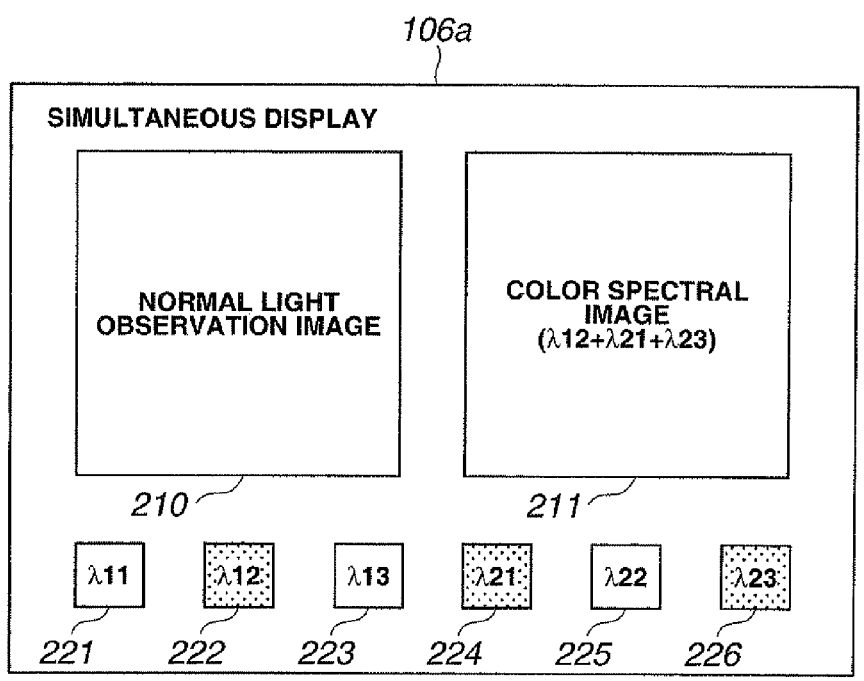
FIG. 22 is a seventh diagram illustrating the graphic user interface with the function of the touch-sensitive panel in FIG. 2.
Figure 23:
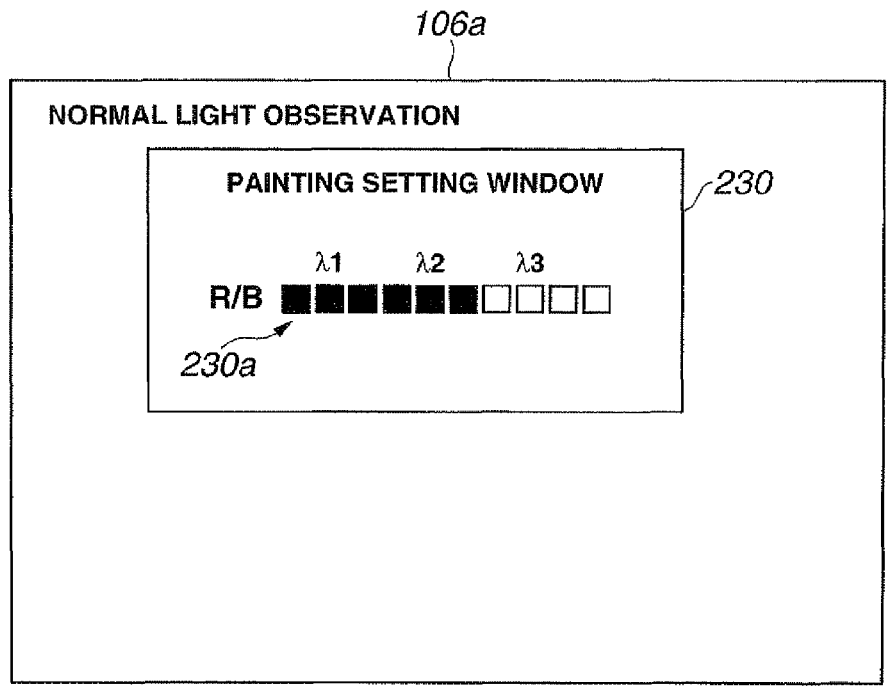
FIG. 23 is an eighth diagram illustrating the graphic user interface with the function of the touch-sensitive panel in FIG. 2.
Figure 24:
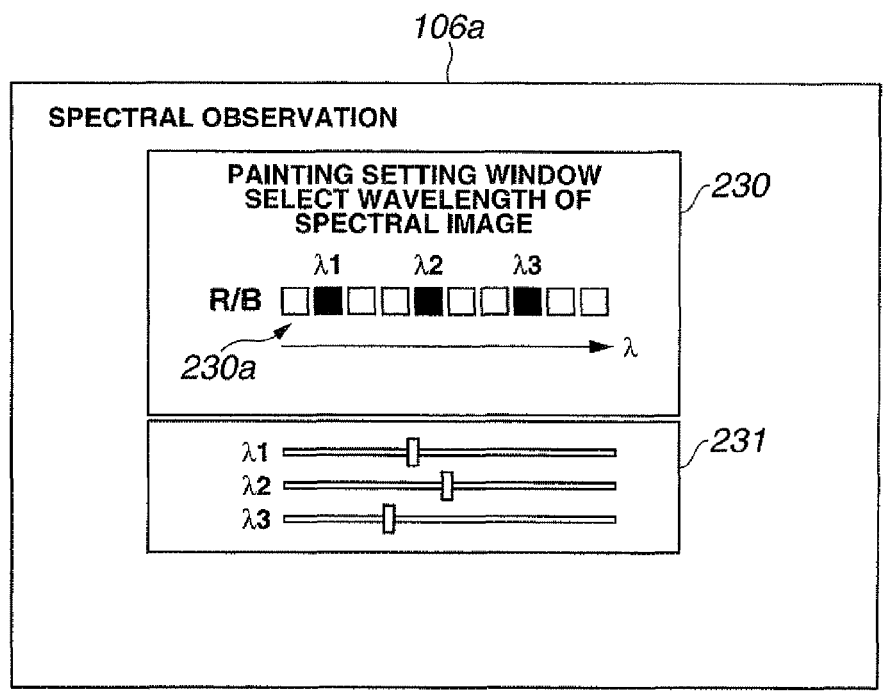
FIG. 24 is a ninth diagram illustrating the graphic user interface with the function of the touch-sensitive panel in FIG. 2.
Figure 25:
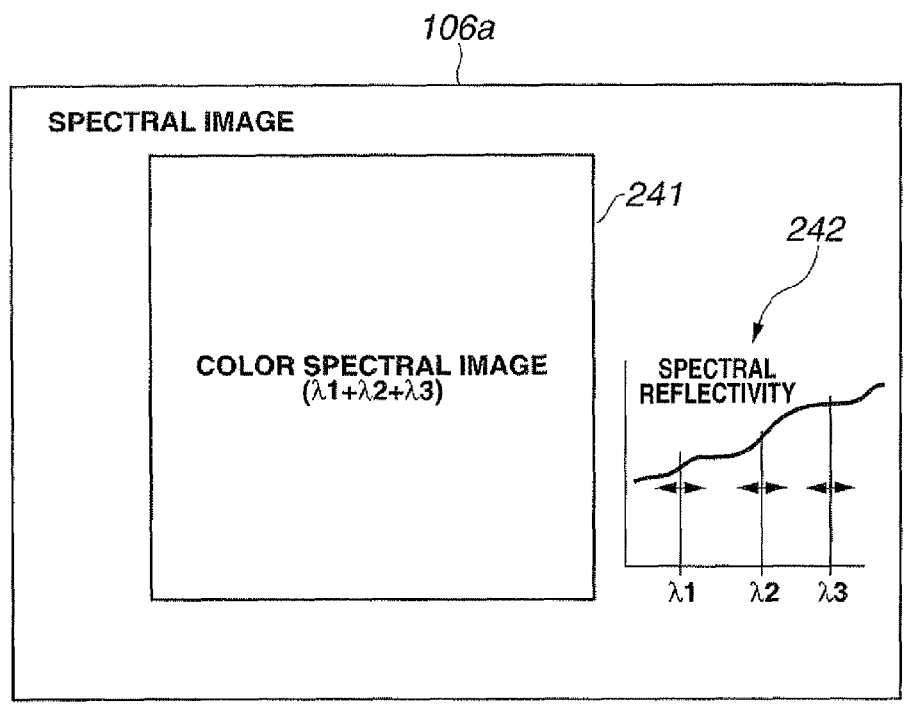
FIG. 25 is a tenth diagram illustrating the graphic user interface with the function of the touch-sensitive panel in FIG. 2.
Figure 26:
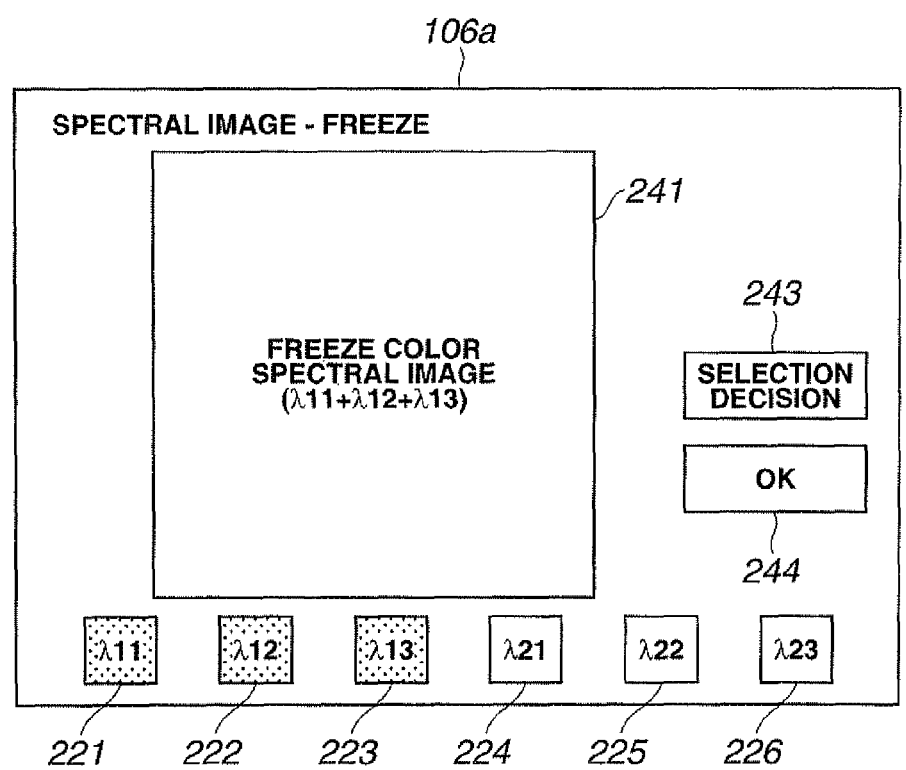
FIG. 26 is an eleventh diagram illustrating the graphic user interface with the function of the touch-sensitive panel in FIG. 2.
Figure 27:
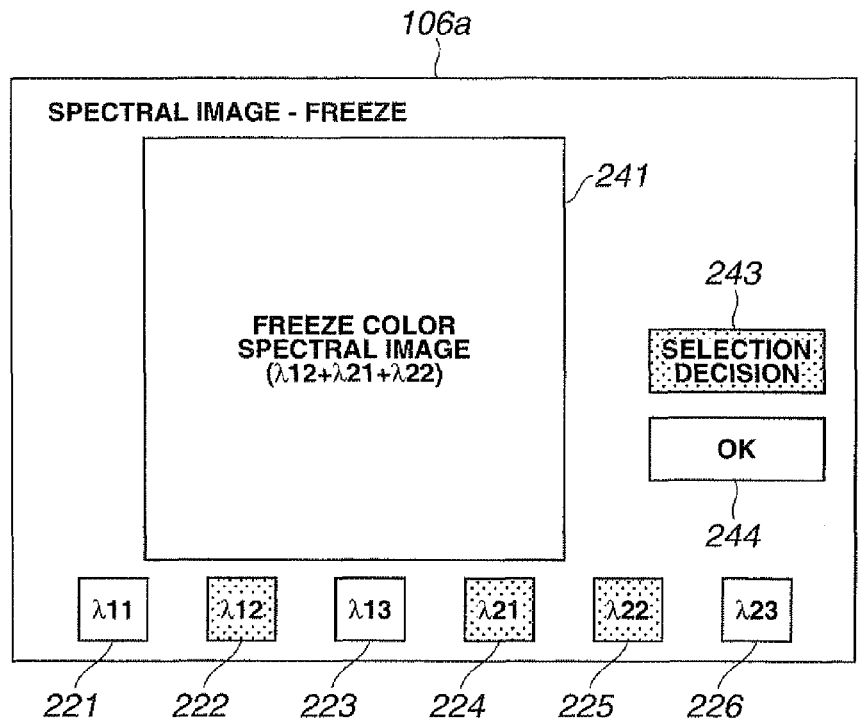
FIG. 27 is a twelfth diagram illustrating the graphic user interface with the function of the touch-sensitive panel in FIG. 2.
Figure 28:
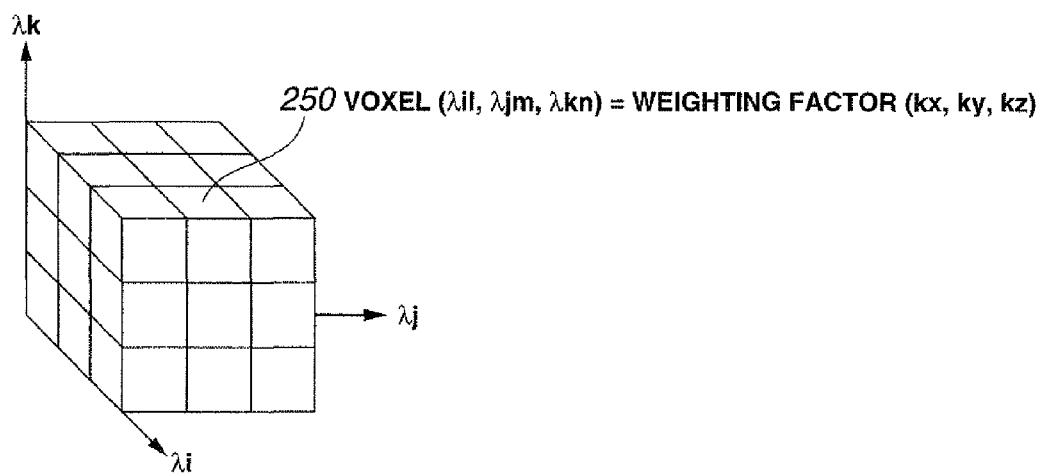
FIG. 28 is a diagram illustrating white balance processing on a spectral image generated by the matrix operation unit in FIG. 2.
Figure 29:
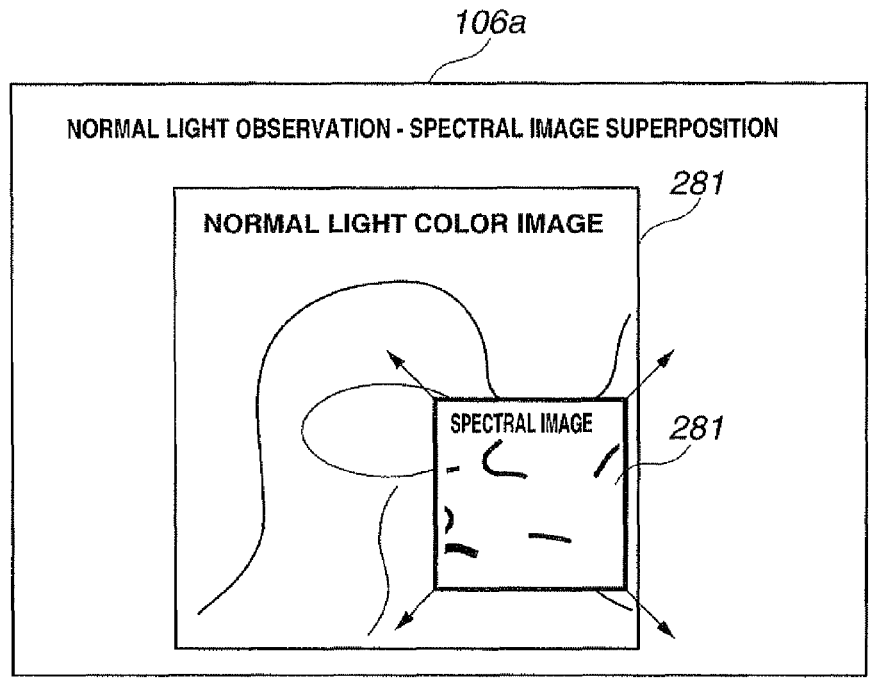
FIG. 29 is a thirteenth diagram illustrating the graphic user interface with the function of the touch-sensitive panel in FIG. 2.
Figure 30:
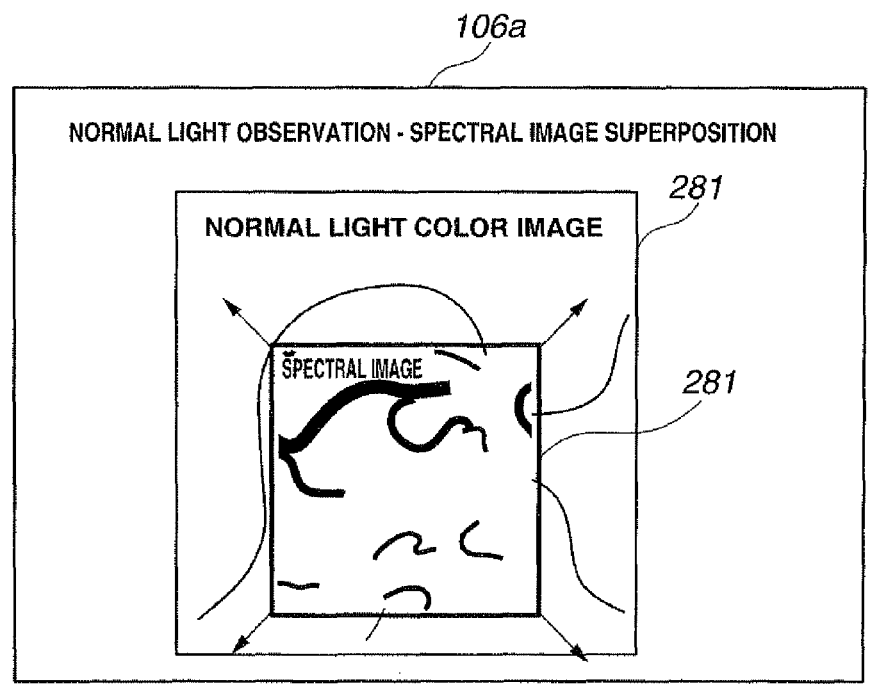
FIG. 30 is a fourteenth diagram illustrating the graphic user interface with the function of the touch-sensitive panel in FIG. 2.

FIG. 21 is a sixth diagram illustrating the graphic user interface with the function of the touch-sensitive panel in FIG. 2; FIG. 22 is a seventh diagram illustrating the graphic user interface with the function of the touch-sensitive panel in FIG. 2; FIG. 23 is an eighth diagram illustrating the graphic user interface with the function of the touch-sensitive panel in FIG. 2; FIG. 24 is a ninth diagram illustrating the graphic user interface with the function of the touch-sensitive panel in FIG. 2; FIG. 25 is a tenth diagram illustrating the graphic user interface with the function of the touch-sensitive panel in FIG. 2; FIG. 26 is an eleventh diagram illustrating the graphic user interface with the function of the touch-sensitive panel in FIG. 2; FIG. 27 is a twelfth diagram illustrating the graphic user interface with the function of the touch-sensitive panel in FIG. 2; FIG. 28 is a diagram illustrating white balance processing on a spectral image generated by the matrix operation unit in FIG. 2; FIG. 29 is a thirteenth diagram illustrating the graphic user interface with the function of the touch-sensitive panel in FIG. 2; and FIG. 30 is a fourteenth diagram illustrating the graphic user interface with the function of the touch-sensitive panel in FIG. 2.

Figure 31:
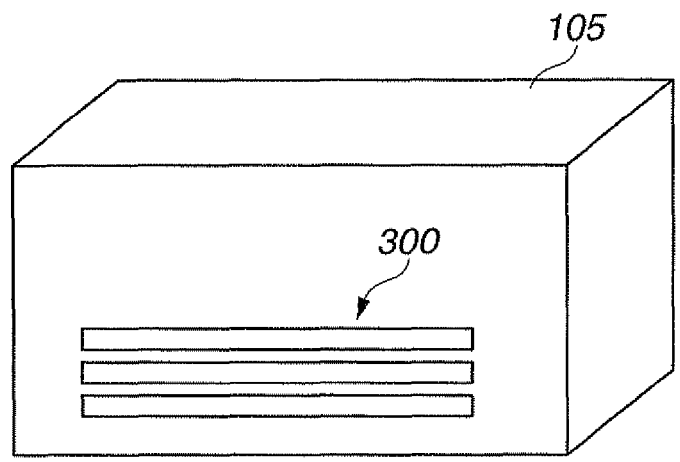
FIG. 31 is a diagram showing configuration of board slots on a back surface of a main body of the endoscope device in FIG. 1.
Figure 32:
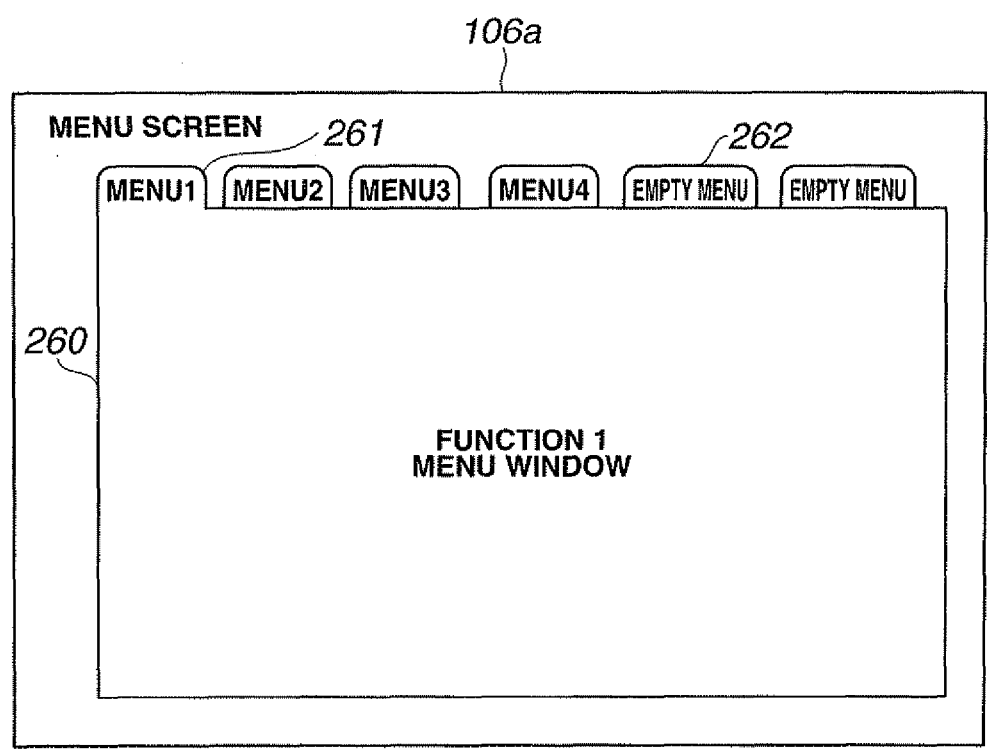
FIG. 32 is a first diagram illustrating an additional function menu of a function expansion substrate inserted into a board slot in FIG. 31.
Figure 33:
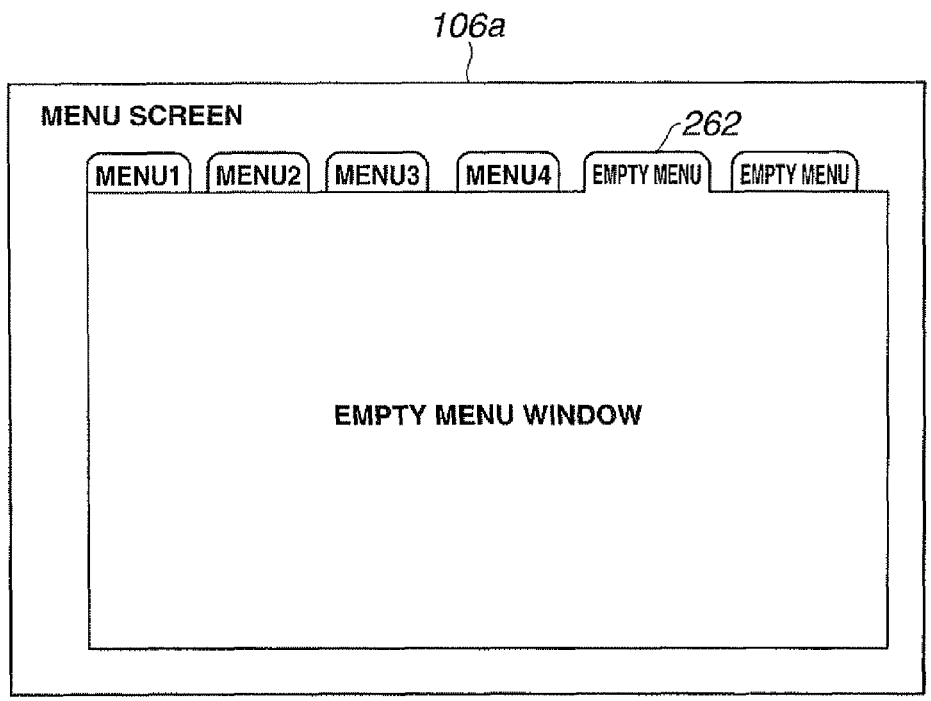
FIG. 33 is a second diagram illustrating an additional function menu of a function expansion substrate inserted into the board slot in FIG. 31.
Figure 34:
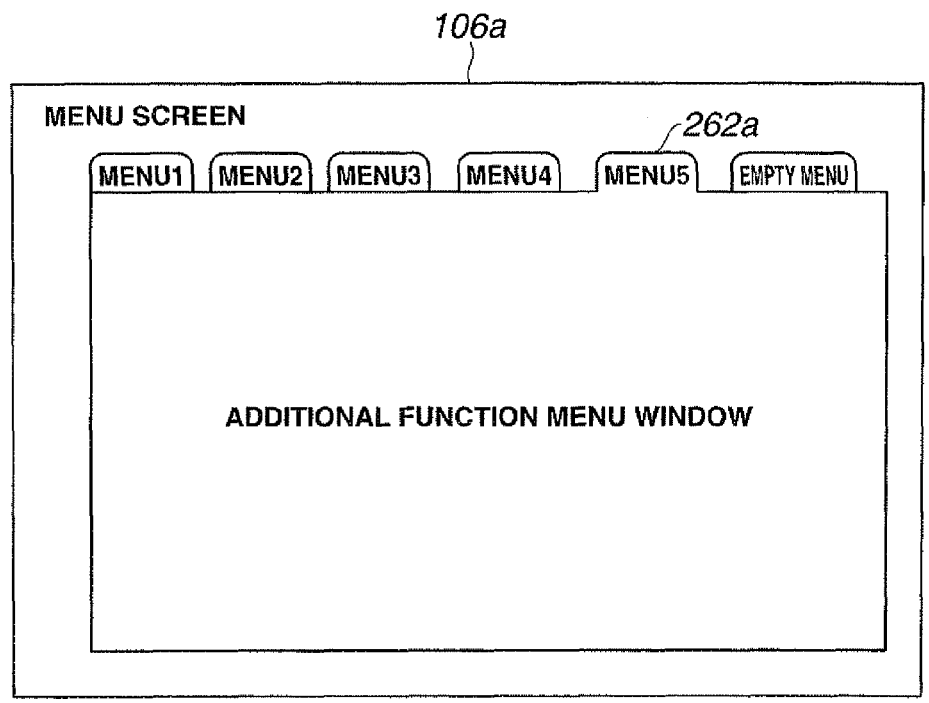
FIG. 34 is a third diagram illustrating an additional function menu of a function expansion substrate inserted into the board slot in FIG. 31.
Figures 35, 36:
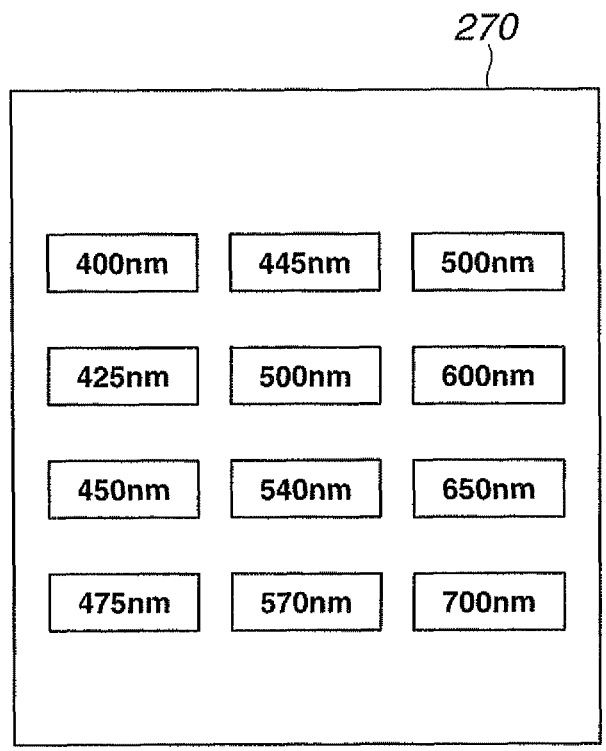
FIG. 35 is a diagram showing one example of a keyboard dedicated to wavelength selection that can be connected to the main body of the endoscope device in FIG. 2.
FIG. 36 is a diagram showing arrangement in a variation of the color filters in FIG. 4.

FIG. 31 is a diagram showing configuration of board slots on a back surface of a main body of the endoscope device in FIG. 1; FIG. 32 is a first diagram illustrating an additional function menu of a function expansion substrate inserted into a board slot in FIG. 31; FIG. 33 is a second diagram illustrating an additional function menu of a function expansion substrate inserted into the board slot in FIG. 31; FIG. 34 is a third diagram illustrating an additional function menu of a function expansion substrate inserted into the board slot in FIG. 31; FIG. 35 is a diagram showing one example of a keyboard dedicated to wavelength selection that can be connected to the main body of the endoscope device in FIG. 2; and FIG. 36 is a diagram showing arrangement in a variation of the color filters in FIG. 4;

In an electronic endoscope device as a living body observation device according to the embodiment of the present invention, light is radiated to a living body being a subject from an illuminating light source, and a solid-state image pickup device being an image pickup unit receives light reflected from the living body based on the radiated light, photoelectrically converts the received light, so that a image pickup signal being a color image signal is generated and a spectral image signal (hereinafter, also simply referred to as a spectral image) being a spectral signal is generated corresponding to an optical wavelength narrowband image, that is, a band image of a discrete spectral distribution of said subject, from the image pickup signal by signal processing.

As shown in FIG. 1, an electronic endoscope device 100 according to the first embodiment includes an endoscope 101 as an observation unit, a main body 105 of the endoscope device and a display monitor 106 as a display device. The endoscope 101 is configured mainly with an insertion unit 102 inserted into a subject body, a distal end unit 103 provided at a distal end of the insertion unit 102, and an angle operation unit 104, being provided on an opposite side of the distal end of the insertion unit 102, for instructing bending operation on the distal end unit 103, for example.

In the main body 105 of the endoscope device, pre-determined signal processing is performed on an image of the subject acquired by the endoscope 101 being a flexible scope, and the display monitor 106 displays a processed image. A display unit of the display monitor 106 is provided with a touch-sensitive panel 106a, which realizes a graphic interface to display various setting screens on the display unit of the display monitor 106, and use a pointing device function of the touch-sensitive panel 106a (hereinafter, referred to as a touch-sensitive panel function).

Next, referring to FIG. 2, the main body 105 of the endoscope device will be described in detail. FIG. 2 is a block diagram of the electronic endoscope device 100.

As shown in FIG. 2, the main body 105 of the endoscope device is configured mainly with a light source unit 41 as an illumination source, a control unit 42 as a signal processing control unit, and a main body processing device 43. The control unit 42 and the main body processing device 43 configure a signal processing control unit for controlling operation of the light source unit 41 and/or a CCD 21 as an image pickup unit, outputting an image signal to the display monitor 106 being a display device, and controlling a touch-sensitive panel function of the touch-sensitive panel 106a. The control unit 42 is connected to a data storage unit 44 for storing various data.

In the description of the present embodiment, the main body 105 of the endoscope device being a single unit includes the light source unit 41 and the main body processing device 43 for image processing, for example. However, the light source unit 41 and the main body processing device 43 can be also configured to be removable as separate units from the main body 105 of the endoscope device.

The light source unit 41 being an illumination source, which is connected to the control unit 42 and the endoscope 101, radiates a pre-determined light quantity of white light (which can be incomplete white light) based on a signal from the control unit 42. The light source unit 41 includes a lamp 15 as a white light source, an infrared cut filter 15a, a light quantity limiting filter 16, being inserted/removed on an optical path, as a spectral characteristics control unit for limiting light quantity in a pre-determined wavelength region of white light, a filter insertion/removal driving unit 17 for inserting/removing the light quantity limiting filter 16 on an optical path, and a condensing lens 18 for outputting white light.

FIG. 3 shows transmission characteristics of the light quantity limiting filter 16. For example, when a transmission rate of a blue band is 100%, the light quantity limiting filter 16 limits transmission rates of other bands to 50%, as shown in FIG. 3.

The endoscope 101 connected to the light source unit 41 via a connector 11 comprises an object lens 19 and a solid-state image pickup device 21 such as a CCD (hereinafter, simply referred to as a CCD) at the distal end unit 103. The CCD 21 according to the present embodiment is a single-panel type (a CCD used for a simultaneous type electronic endoscope) and a primary color type. FIG. 4 shows arrangement of color filters arranged on an image pickup surface of the CCD 21. The color filters arranged on the image pickup surface of the CCD 21 configure a color separation unit.

As shown in FIG. 2, the insertion unit 102 contains a light guide 14 for guiding light radiated from the light source unit 41 to the distal end unit 103, a signal line for transmitting an image of a subject obtained by the CCD 21 to the main body processing device 43, a forceps channel 28 for treatment and the like. A forceps hole 29 for inserting forceps into the forceps channel 28 is provided in a vicinity of the operation unit 104.

The operation unit 104 contains an ID unit 110 for storing classification information of the endoscope 101. The operation unit 104 is also provided with an instruction switch unit 111 for instructing various operations on an outer surface. The instruction switch unit 111 includes at least a mode changing switch for instructing a spectral image generation mode, which will be described later, to generate a spectral image with improved S/N.

The main body processing device 43 as a signal processing device for a living body observation device is connected to the endoscope 101 via the connector 11 similarly to the light source unit 41. The main body processing device 43 contains a CCD drive 431 for driving the CCD 21 in the endoscope 101. The main body processing device 43 also includes a luminance signal processing system and a color signal processing system as signal circuit systems for obtaining a color image being a normal image.

The luminance signal processing system of the main body processing device 43 includes a contour correction unit 432, being connected to the CCD 21, for correcting a contour of an image pickup signal from the CCD 21, and a luminance signal processing unit 434 for generating a luminance signal from data corrected by the contour correction unit 432. The color signal processing system of the main body processing device 43 also includes sample hold circuits (S/H circuits) 433a to 433c, being connected to the CCD 21, for sampling an image pickup signal obtained by the CCD 21, for example, to generate an RGB signal, and a color signal processing unit 435, being connected to outputs of the S/H circuits 433a to 433c, for generating a color signal.

The main body processing device 43 also includes a normal image generation unit 437 for generating a color image being a single normal image from the outputs of the luminance signal processing system and the color signal processing system. The normal image generation unit 437 outputs a Y signal being a luminance signal and an R-Y signal and a B-Y signal being color difference signals to a display image generation unit 439, and generates a normal image signal of a color image being a normal image displayed on the display monitor 106 by the display image generation unit 439 based on the Y signal, R-Y signal and B-Y signal.

Meanwhile, the main body processing device 43 includes a matrix operation unit 436 as a spectral signal generation unit for performing a pre-determined matrix operation on an RGB signal to which, as a signal circuit system for obtaining a spectral image signal being a spectral signal, outputs (RGB signals) of the S/H circuits 433a to 433c are inputted. The matrix operation by the matrix operation unit 436 is processing to perform addition processing, for example, on color image signals, and multiply a matrix obtained by a matrix calculation method described later.

In the present embodiment, a method using electronic circuit processing (processing by hardware with an electronic circuit) will be described as a method for the matrix operation. However, a method can be also possible using numerical data processing (processing by software with a program). For implementation, a combination of the methods is also possible.

Spectral image signals F1 to F3 being output of the matrix operation unit 436 are subjected to color adjustment operation in a color adjustment unit 440 being a color adjustment unit to generate spectral color channel image signals Rch, Gch and Bch from the spectral image signals F1 to F3. The generated spectral color channel image signals Rch, Gch and Bch are sent to RGB color channels R-(ch), G-(ch) and B-(ch) of the display monitor 106 via the display image generation unit 439.

The display image generation unit 439 generates a display image including a normal image and/or a spectral image and outputs the display image on the display monitor 106, and can display spectral images by switching between the images. That is, an operator can selectively display any of a normal image, a spectral color channel image through the color channel R-(ch), a spectral color channel image through the color channel G-(ch) and a spectral color channel image through the color channel B-(ch) on the display monitor 106. The display monitor 106 can also be configured to be able to simultaneously display any two or more images. Particularly, if a normal image and a spectral color channel image (hereinafter, also referred to as a spectral channel image) can be simultaneously displayed, a normal image for general observation and a spectral channel image can be easily compared, so that observation is possible in consideration of their respective features (a normal image has a feature of a color degree being similar to normal macroscopic observation and can be observed easily; and a spectral channel image has a feature that a pre-determined blood vessel, for example, can be observed that cannot be observed with a normal image), which is very useful to diagnosis.

The following will describe a matrix calculation method for the matrix operation unit 436 to calculate a matrix.

(Matrix Calculation Method)

FIG. 5 is a conceptual diagram showing a flow of a signal in generating a spectral image signal corresponding to an image being more approximately equivalent to an optical wavelength narrowband image from color image signals (referred to as R, G and B herein for ease of description; however, combination of G, Cy, Mg and Ye is also possible in a complementary solid-state image pickup device, as described later). Hereinafter, a vector and a matrix are represented in a bold character or with " " (for example, a matrix A is represented as "A (bold character)", or "A"), while others are represented without character decoration.

First, the electronic endoscope device 100 converts color sensitivity characteristics as spectral sensitivity characteristics of respective R, G and B image pickup units into numerical data. The R, G and B color sensitivity characteristics are output characteristics for wavelengths obtained when an image of a white shooting object is picked up using a white-light source.

The respective R, G and B color sensitivity characteristics are shown in right of image data as a simplified graph. In the graph, the R, G and B color sensitivity characteristics are represented as n-dimensional column vectors "R", "G" and "B", respectively.

Next, the electronic endoscope device 100 converts characteristics of narrowband bandpass filters F1, F2 and F3 for a spectral image with center wavelengths λ1, λ2 and λ3 (for example, λ1=420 nm, λ2=540 nm and λ3=605 nm) as basic spectral characteristics of spectral signals to be extracted, for example, three spectral signals into numerical data. Characteristics of the filters are represented as n-dimensional column vectors "F1", "F2" and "F3", respectively.

Based on the acquired numerical data, an optimal coefficient set is obtained to approximate a following relation. That is, matrix elements satisfying

[Formula 1]

$$(R \; G \; B) \begin{pmatrix} a_1 & a_2 & a_3 \\ b_1 & b_2 & b_3 \\ c_1 & c_2 & c_3 \end{pmatrix} = (F_1 \; F_2 \; F_3) \quad (1)$$

should be obtained.

A solution to a proposition of the above optimization is mathematically given as follows: when a matrix representing R, G and B color sensitivity characteristics is "C", a matrix representing spectral characteristics of a narrowband bandpass filter to be extracted is "F", and a coefficient matrix to be obtained which executes principal component analysis or orthogonal development (or orthogonal transformation) is "A":

[Formula 2]

$$C = \begin{pmatrix} R & G & B \end{pmatrix} \quad A = \begin{pmatrix} a_1 & a_2 & a_3 \\ b_1 & b_2 & b_3 \\ c_1 & c_2 & c_3 \end{pmatrix} \quad F = \begin{pmatrix} F_1 & F_2 & F_3 \end{pmatrix} \quad (2)$$

Therefore, the proposition shown in the expression (1) is equal to that to obtain the matrix "A" satisfying a following relation:
[Formula 3]

$$CA = F \quad (3)$$

where for a point sequence number n as spectrum data representing spectral characteristics, n>3, so that the expression (3) is given not as a one-dimensional simultaneous equation, but as a solution to a linear least-squares method. That is, a quasi-inverse matrix can be solved from the expression (3). When a transposed matrix of the matrix "C" is "tC", the expression (3) is as follows:
[Formula 4]

$${}^tCCA = {}^tCF \quad (4)$$

where "tCC" is an n×n square matrix. Therefore, the expression (4) can be considered as a simultaneous equation of the matrix "A". A solution to the equation is given as follows:
[Formula 5]

$$A = ({}^tCC)^{-1}{}^tCF \quad (5)$$

The electronic endoscope device 100 converts a left-hand side of the expression (3) for the matrix "A" obtained by the expression (5) and can approximate characteristics of the narrowband bandpass filters F1, F2 and F3 to be extracted.

The matrix operation unit 436 generates a spectral image signal from a normal color image signal using the matrix calculated as the above.

Next, operation of the electronic endoscope device 100 according to the present embodiment will be described in detail referring to FIG. 2.

In the following, operation of normal image generation will be described first, and operation of spectral image generation will be described later.

Normal Image Generation:

First, operation of the light source unit 41 will be described. Based on a control signal from the control unit 42, the filter insertion/removal driving unit 17 sets the light quantity limiting filter 16 out of a position on an optical path. Light flux from the lamp 15 is condensed at an inlet end of the light guide 14 being an optical fiber bundle provided in the connector 11 at a connection unit between the endoscope 101 and the light source unit 41 by the condensing lens 18 via the infrared cut filter 15a without transmitting through the light quantity limiting filter 16.

The condensed light flux is radiated into a body of a subject from an illumination optical system provided at the distal end unit 103 through the light guide 14. The radiated light flux reflects in the subject and signals are collected for each color filter shown in FIG. 4 in the CCD 21 via the object lens 19.

The collected signals are inputted to the above luminance signal processing system and color signal processing system in parallel. The signals collected for each color filter are added and inputted to the contour correction unit 432 of the luminance signal system for each pixel, and inputted to the luminance signal processing unit 434 after contour correction. Luminance signals are generated in the luminance signal processing unit 434, and inputted to the normal image generation unit 437.

Meanwhile, the signals collected by the CCD 21 are inputted to the S/H circuits 433a to 433c for each filter, and R, G and B signals are generated. Further, the color signal processing unit 435 generates color signals from the R, G and B signals. The normal image generation unit 437 generates Y signals, R-Y signals and B-Y signals from the luminance signals and color signals. The display image generation unit 439 displays a normal image of the subject on the display monitor 106.

Spectral Image Generation:

Spectral image generation has two generation modes. A first spectral image generation mode is a mode to prevent light flux from the lamp 15 from being transmitted through the light quantity limiting filter 16 similarly to the normal image generation. A second spectral image generation mode is a mode to cause light flux from the lamp 15 to transmit through the light quantity limiting filter 16. In a default state, the control unit 42 sets a spectral image generation mode to the first spectral image generation mode. When a mode changing switch of the instruction switch unit 111 is operated, the control unit 42 controls driving of the filter insertion/removal driving unit 17, arranges the filter insertion/removal driving unit 17 on an optical path of light flux from the lamp 15, and sets the generation mode to the second spectral image generation mode. As a result, in the second spectral image generation mode, the light flux from the lamp 15 will be transmitted through the light quantity limiting filter 16.

In the present embodiment, the spectral image generation mode can be also set to the second spectral image generation mode by operating a keyboard or the touch-sensitive panel 106a provided on the main body 105 instead of the mode changing switch of the instruction switch unit 111. The first spectral image generation mode and the second spectral image generation mode are same in other operation, so the description will take the first spectral image generation mode as an example. Similar operation to the normal image generation will not be described.

During the spectral image generation in the first spectral image generation mode, the matrix operation unit 436 amplifies and adds outputs (ROB signals) of the S/HE circuits 433a to 433c. The color adjustment unit 440 performs color adjustment operation on the spectral image signals F1 to F3 being outputs of the matrix operation unit 436 and the spectral color channel image signals Rch, Gch and Bch are generated from the spectral image signals F1 to F3. The generated spectral color channel image signals Rch, Gch and Bch are sent to the ROB color channels R-(ch), G-(ch) and B-(ch) of the display monitor 106.

In the above way, the main body processing device 43 can display a spectral image corresponding to a narrowband light observation image obtained with narrowband light via narrowband bandpass filters F1, F2 and F3 with center wavelengths λ1, λ2 and λ3 as shown in FIG. 6 on the display monitor 106.

The following illustrates one example of a spectral image generated using the quasi-filter characteristics corresponding to the narrowband bandpass filters F1, F2 and F3.

As shown in FIG. 7, tissue in a body cavity 51 often has absorber distribution structures such as different blood vessels in a depth direction, for example. Many capillary vessels 52 distribute around a mucosa surface layer, blood vessels 53, which are larger than the capillary vessels, distribute in addition to the capillary vessels in an intermediate layer being deeper than the mucosa surface layer, and further larger blood vessels 54 distribute in a further deeper layer.

On the other hand, an invasion depth of light in a depth direction into the tissue in the body cavity 51 depends on a wavelength of the light. For illumination light including a visible region, short wavelength light like blue (B) light as shown in FIG. 8 only invades near a surface layer due to absorption characteristics and scattering characteristics in living tissue, is absorbed and scattered in that depth range, and light emitted from the surface is observed. Green (G) light of a longer wavelength than blue (B) light invades deeper than the range in which blue (B) light invades, is absorbed and scattered in that range, and light emitted from the surface is observed. Red (R) light of a longer wavelength than green (G) light reaches a deeper range.

As shown in FIG. 9, since respective wavelength regions of RGB light in normal observation of the tissue in a body cavity 51 overlap, (1) An image pickup signal subjected to image pickup by the CCD 21 through B-band light picks up a band image with superficial layer and intermediate layer tissue information containing much tissue information in a superficial layer as shown in FIG. 10,
(2) An image pickup signal subjected to image pickup by the CCD 21 through G-band light picks up a band image with superficial layer and intermediate layer tissue information containing much tissue information in an intermediate layer as shown in FIG. 11, and
(3) An image pickup signal subjected to image pickup by the CCD 21 through R-band light picks up a band image with intermediate layer and deep layer tissue information containing much tissue information in a deep layer as shown in FIG. 12.

The main body 105 of the endoscope device performs signal processing on the KGB image pickup signals, so that an endoscope image can be obtained in which color is reproduced as desired or naturally as an endoscope image.

The above matrix processing in the matrix operation unit 436 is to create a spectral image signal by using a quasi-bandpass filter (matrix) previously generated as the above for a color image signal. For example, the spectral image signals F1 to F3 are obtained using the quasi-bandpass filters F1 to F3 with discrete and narrowband spectral characteristics that can extract the desired deep layer tissue information as shown in FIG. 6. Since respective wavelength regions of the quasi-bandpass filters F1 to F3 do not overlap as shown in FIG. 6, (4) A spectral image signal F1 through the quasi-bandpass filter F1 picks up a band image with the tissue information in the superficial layer as shown in FIG. 13,
(5) A spectral image signal F2 through the quasi-bandpass filter F2 picks up a band image with the tissue information in the intermediate layer as shown in FIG. 14, and
(6) A spectral image signal F3 through the quasi-bandpass filter F3 picks up a band image with the tissue information in the deep layer as shown in FIG. 15.

For the spectral image signals F1 to F3 acquired in the above manner, the color adjustment unit 440 assigns the spectral image signal F3 to the spectral color channel image signal Rch, the spectral image signal F2 to the spectral color channel image signal Gch, and the spectral image signal F1 to the spectral color channel image signal Bch, as an example of simplest color conversion, and outputs the signals to the RGB color channels R-(ch), G-(ch) and B-(ch) of the display monitor 106 via the display image generation unit 439.

If a color image through the color channels R-(ch), G-(ch) and B-(ch) is observed on the display monitor 106, it appears as an image as shown in FIG. 16, for example. Large blood vessels are at deeper positions, the spectral image signal F3 is reflected, and a color image having pre-determined target colors is shown as a red pattern. For a vascular network near an intermediate layer, the spectral image signal F2 is strongly reflected, so that a color image having pre-determined target colors is shown as a magenta pattern. Some of the vascular networks near a mucosa surface are expressed as yellow patterns.

The spectral image signals F1 to F3 depend on spectral sensitivity of an endoscope such as a lens or an opto-electric conversion system in addition to spectral reflectivity of a shooting object. As such, the control unit 42 reads out an ID being classification information of the endoscope 101 from the ID unit 110 in the operation unit 104, and corrects the spectral image signals F1 to F3 with a correction coefficient depending on the connected endoscope 101 stored in the data storage unit 44 based on the ID. The present embodiment can be configured such that a correction coefficient is stored in the ID unit 110 and the control unit 42 reads out an ID and the correction coefficient from the ID unit 110.

As described in the above, the spectral image signals F1 to F3 are generated through matrices corresponding to the quasi-bandpass filters F1 to F3, while the quasi-bandpass filters F1 to F3 are characterized by center wavelengths $\lambda 1$, $\lambda 2$ and $\lambda 3$. That is, the main body processing device 43 sets one center wavelength $\lambda$ to decide one quasi-bandpass filter F, and generates a spectral image signal F based on the quasi-bandpass filter F.

According to the present embodiment, a function of the touch-sensitive panel 106a can be used to set a center wavelength $\lambda$ by a graphic user interface and generate a desired spectral image signal F.

The following will describe the graphic user interface by the function of the touch-sensitive panel 106a.

According to the present embodiment, the main body processing device 43 displays a setting screen to set a center wavelength of a quasi-bandpass filter corresponding to a spectral image signal on the observation monitor 106 including the touch-sensitive panel 106a as in FIG. 17. The setting screen can set a plurality of for example, six center wavelengths $\lambda 11$, $\lambda 12$, $\lambda 13$, $\lambda 21$, $\lambda 22$ and $\lambda 23$, For example, if a $\lambda 11$ button 201 for starting setting the wavelength $\lambda 11$ is selected using a touch-sensitive panel function, the main body processing device 43 deploys and displays a pop-up window 207 having a plurality of selectable wavelengths on the observation monitor 106. Then, a set wavelength value of the pop-up window 207 is selected through the touch-sensitive panel function, so that the main body processing device 43 sets the set wavelength value as the wavelength $\lambda 11$. FIG. 17 indicates a state of the main body processing device 43 having set a set wavelength value 425 nm as the wavelength $\lambda 11$. Operations to set other wavelengths, i.e., a $\lambda 12$ button 202, a $\lambda 13$ button 203, a $\lambda 21$ button 204, a $\lambda 22$ button 205 and $\lambda 23$ button 206 can also set wavelength values to be set using the touch-sensitive panel function on the setting screen similarly to the wavelength $\lambda 11$. A spectral image can be colored by setting set wavelength values as at least three wavelengths (for example, the wavelengths $\lambda 11$, $\lambda 12$ and $\lambda 13$) on the setting screen. Hereinafter, a colored spectral image is referred to as a color spectral image.

According to the present embodiment, the setting screen to set a center wavelength of a quasi-bandpass filter is not limited to as shown in FIG. 17, but can be a setting screen including a set table 208 to set a plurality of wavelength sets in which three wavelengths constitutes a set for previous coloring as shown in FIG. 18 as a first variation of the present embodiment. If the setting screen in FIG. 18 is displayed on the observation monitor 106 including the touch-sensitive panel 106a, a desired wavelength set can be selected from the plurality of wavelength sets being set in the set table 208 using the touch-sensitive panel function.

Alternatively, a select button 209 can be provided, the set table 208 can be set by toggling the wavelength sets at each time the select button 209 is operated using the touch-sensitive panel function as shown in FIG. 19 as a second variation of the present embodiment. Specifically, each time the select button 209 is operated using the touch-sensitive panel function, a set to be set is toggled for selection as in set 1→set 2→set 3→set 4→set 1→ . . . . FIG. 20 shows the setting screen when the select button 209 is operated using the touch-sensitive panel function in the state in FIG. 19, selection of the set 1 as shown in FIG. 19 shifts to selection of the set 2 as shown in FIG. 20 through an operation of the select button 209.

According to the present embodiment, the display image generation unit 439 has display forms to display a color spectral image on the display screen of the touch-sensitive panel 106a (i.e., the observation monitor 106) such as: (1) a display form to simultaneously display a normal light observation image and a color spectral image; (2) a display form to display only a color spectral image; and (3) a display form to display only a normal light observation image.

In the form to simultaneously display a normal light observation image and a spectral color image, the main body processing device 43 can simultaneously display a normal light observation image 210 and a colored color spectral image 211 on the observation monitor 106 by the display image generation unit 439, as shown in FIG. 21. During the above, the display image generation unit 439 can display thumbnail images 221 to 226 of spectral images with the six center wavelengths being set in, for example, the above setting screen available to be used in coloring the color spectral image 211 in addition to the normal light observation image 210 and the color spectral image 211. Then, thumbnail images of three spectral images configuring the color spectral image 211 are displayed in a different display form (for example, luminance or color tone) from other thumbnail images. According to the present embodiment, three spectral images can be arbitrarily changed that configure the color spectral image 211 by selecting any of the thumbnail images 221 to 226 using the touch-sensitive panel function. Specifically, for example when the color spectral image 211 is touched, the thumbnail images 221 to 226 are selectable, and three spectral images are changed that configure the color spectral image 211 by selecting thumbnail images of spectral images with three center wavelengths for coloring. FIG. 21 shows a state of the color spectral image 211 being generated through three spectral images with the center the wavelengths λ11, λ12 and λ13. FIG. 22 shows a state of the color spectral image 211 being generated through three spectral images with the center wavelengths λ12, λ21 and λ23.

If the touch-sensitive panel 106a displays only a normal light image as shown in FIG. 23, the main body processing device 43 can display a painting setting window 230 to change a color tone of the normal light image by superposition. The device 43 can change the color tone of the normal light image by the user touching an indicator 230a of the painting setting window 230 using the touch-sensitive panel function to change a ratio of red to blue.

In the display form to display only a color spectral image, the painting setting window 203 is available as a wavelength selection window 230 for a center wavelength λ, as shown in FIG. 24. When the window 230 is used as the wavelength selection window 230, the indicator 230a shows wavelengths, each display point of the indicator 230a is assigned with a plurality of center wavelengths, three spectral images configuring the color spectral image 211 can be selected in the wavelength selection window 230 by selecting three display points in the indicator 230a. When three spectral images are selected, a luminance setting window 231 to set luminance of a spectral image is displayed below the wavelength selection window 230, so that luminance of a spectral image with each wavelength can be arbitrarily set.

In the display form to display only a color spectral image, the main body processing device 43 can display spectral reflectivity 242 from a subject in a vicinity of a color spectral image 241 as a graph, as shown in FIG. 25. For example, the wavelengths λ1, λ2 and λ3 of three spectral images configuring the color spectral image 241 are presented on the spectral reflectivity 242, the wavelengths λ1, λ2 and λ3 can vary through the touch-sensitive panel function; when the wavelengths λ1, λ2 and λ3 vary, the three spectral images configuring the color spectral image 241 change accordingly.

When a freeze switch (not shown) of the instruction switch unit 111 provided in the operation unit 104 of the endoscope 101, for example, is operated in the display form to display only a color spectral image, a color spectral image being displayed as a moving image becomes the static freeze color spectral image 241, as shown in FIG. 26. The main body processing device 43 displays thumbnail images 221 to 226 of the spectral images with the six center wavelengths being set in, for example, the above setting screen available to be used in coloring the freeze color spectral image 241 in a vicinity of the freeze color spectral image 241. Moreover, the thumbnail images of the three spectral images configuring the freeze color spectral image 241 are displayed in a different display form (for example, different luminance or color tone) from other thumbnail images. According to the present embodiment, three spectral images configuring the freeze color spectral image 241 can be arbitrarily changed by selecting the thumbnail images 221 to 226 using the touch-sensitive panel function and operating a selection decision button 243 as shown in FIG. 27. Further, according to the present embodiment, the color spectral image 241 of a moving image of the three spectral images selected from the thumbnail images 221 to 226 can be displayed by operating a confirmation button 244 using the touch-sensitive panel function. According to the present embodiment, the color spectral image 241 of the moving image of the three spectral images selected from the thumbnail images 221 to 226 can also be automatically displayed only by an operation of the selection decision button 243, instead of providing the confirmation button 244.

As described in the above, according to the present embodiment, the main body 105 of the endoscope device can arbitrarily change three spectral images configuring a color spectral image. In that case, white balance processing for the three spectral images is changed simultaneously. In particular, the main body 105 of the endoscope device discretely stores a three-dimensional data table with three wavelengths λi, λj and λk as axes as shown in FIG. 28 previously in the data storage unit 44, for example. Each voxel of the three-dimensional data table stores weighting factors (kx, ky, kz) used for the white balance processing as voxel data. The main body 105 of the endoscope device performs the white balance processing on three spectral images Fl, Fm and Fn with wavelengths λil, λjm and λkn through an operation "color spectral image=kx×Fl+ky×Fm+kz×Fn", for example.

The main body 105 of the endoscope device discretely stores the three-dimensional data table to reduce a storage capacity of the data storage unit 44 for storing respective voxel data. As such, the weighting factors among the voxel data are calculated through general linear interpolation for the white balance processing.

In the display form to display only a normal light observation image, the main body processing device 43 designates a spectral image display frame 281 on the normal light observation image 210 as shown in FIG. 29, so that the device 43 can display a spectral image of the region by superposition in a region of the designated spectral image display frame 281. A size and position of the spectral image display frame 281 can be arbitrarily changed by the touch-sensitive panel function, as shown in FIG. 30.

According to the present embodiment, configuration of a spectral image is set using a wavelength as a setting parameter, but the present invention is not limited thereto. Instead, the designation can be done using depth information being an invasion depth of light as a setting parameter, or the designation can be done using a function name such as blood vessel highlighting as a setting parameter.

Further, according to the present embodiment, configuration of a spectral image being optimal to observation based on an organ to be observed can be automatically designated. In that case, a method of designating configuration of a spectral image based on an organ includes a method of identifying and designating an organ for which the endoscope 101 is used with an ID from the ID unit 110 in the operation unit 104, a method of designating by a menu switch on the touch-sensitive panel 106*a*, a method of designating by reading data of a PC card recording patient information, or a method of automatically recognizing an organ by performing image processing on a normal light observation image by a scene understanding module, for example.

The main body 105 of the endoscope device according to the present embodiment is provided with a plurality of board slots 300 on a back surface into which function expansion substrates for function expansion can be inserted, as shown in FIG. 31. Meanwhile, the control unit 42 displays a menu window 260 as shown in FIG. 32 on the touch-sensitive panel 106*a* to deploy executable functions. Assume that default functions of the control unit 42 without a function expansion substrate being inserted can be classified to four basic functions, for example, the functions are switchable using tags 261 of menus 1, 2, 3 and 4 on the menu window 260. The menu window 260 includes menu tags 262 for a plurality of function expansion substrates in addition to the tags 261 of menus 1, 2, 3 and 4. When no function expansion substrate is set in the board slots 300 as default, the menu tags 262 are for empty menus, as shown in FIG. 33. However, when a function expansion substrate is inserted into the board slots 300, the control unit 44 can deploy an additional function menu window of functions of the inserted function expansion substrate from the menu window 260 through a tag 262*a* of a menu 5, as shown in FIG. 34.

The additional function menu window is configured in software. As such, when a function expansion substrate is inserted, the control unit 42 identifies the function expansion substrate, and a menu window with similar configuration to the basic functions is automatically generated, so that a version of software does not need to be changed, or a version of the software is easily upgraded.

According to the present embodiment, the operation is performed through the touch-sensitive panel 106*a*, and specifications can be easily changed without changing hardware, but by upgrading a version of the software.

According to the present embodiment, not all of the operations must be performed through the touch-sensitive panel 106*a*, but the operations can be performed using a pointing device such as a trackball or mouse, or a wavelength of a spectral image can be set through a keyboard 270 dedicated to select a wavelength, for example, as shown in FIG. 35. Moreover, a wavelength setting function can be assigned to a function key of a general keyboard.

As described in the above, according to the present embodiment, in a default state of a spectral image generation mode being the first spectral image generation mode, the display monitor 106 can selectively display a normal light observation image and a spectral image by prioritizing a image quality of a normal light observation image. Further, the mode changing switch of the instruction switch unit 111 switches the spectral image generation mode to the second spectral image generation mode through operation, transmit light flux from the lamp 15 through the light quantity limiting filter 16, and decreases light quantity of light in other wavelength bands to a half of light in a blue wavelength band, so that the display monitor 106 can selectively display the normal light observation image and the spectral image by prioritizing image quality of a spectral image.

In other words, by setting the spectral image generation mode to the second spectral image generation mode, and transmitting light flux from the lamp 15 through the light quantity limiting filter 16, a spectral image in a blue wavelength band can be improved to image information with a similar S/N to spectral images in other wavelength bands, for example.

According to the present embodiment, the light quantity limiting filter 16 is configured to be insertably removable on an optical path. However, the filter 16 can also be permanently provided on an optical path. Moreover, a color filter provided for the CCD 21 can have similar spectral characteristics to a light quantity limiting filter, thereby omitting the light quantity limiting filter 16.

As a variation of the present embodiment, complementary color filters can be used instead of using the RGB primary color filters. Arrangement of the complementary filters is configured with G, Mg, Ye and Cy elements as shown in FIG. 36. A relation between the respective elements of the primary color filters and the respective elements of the complementary color filters is: Mg=R+B, Cy=G+B and Ye=R+G.

According to the variation, all pixels of the CCD 21 are read out, and signal processing or image processing is performed on an image from each color filter. If the complementary filters are used, it is needless to say that the S/H circuit shown in FIG. 2 is not for R, C and B, but for G, Mg, Cy and Ye, but living body spectral reflectivity can be approximated with three basic spectral characteristics for four or less units. Accordingly, a dimension to calculate an estimated matrix is changed from three to four.

(Second Embodiment)

Figure 37:
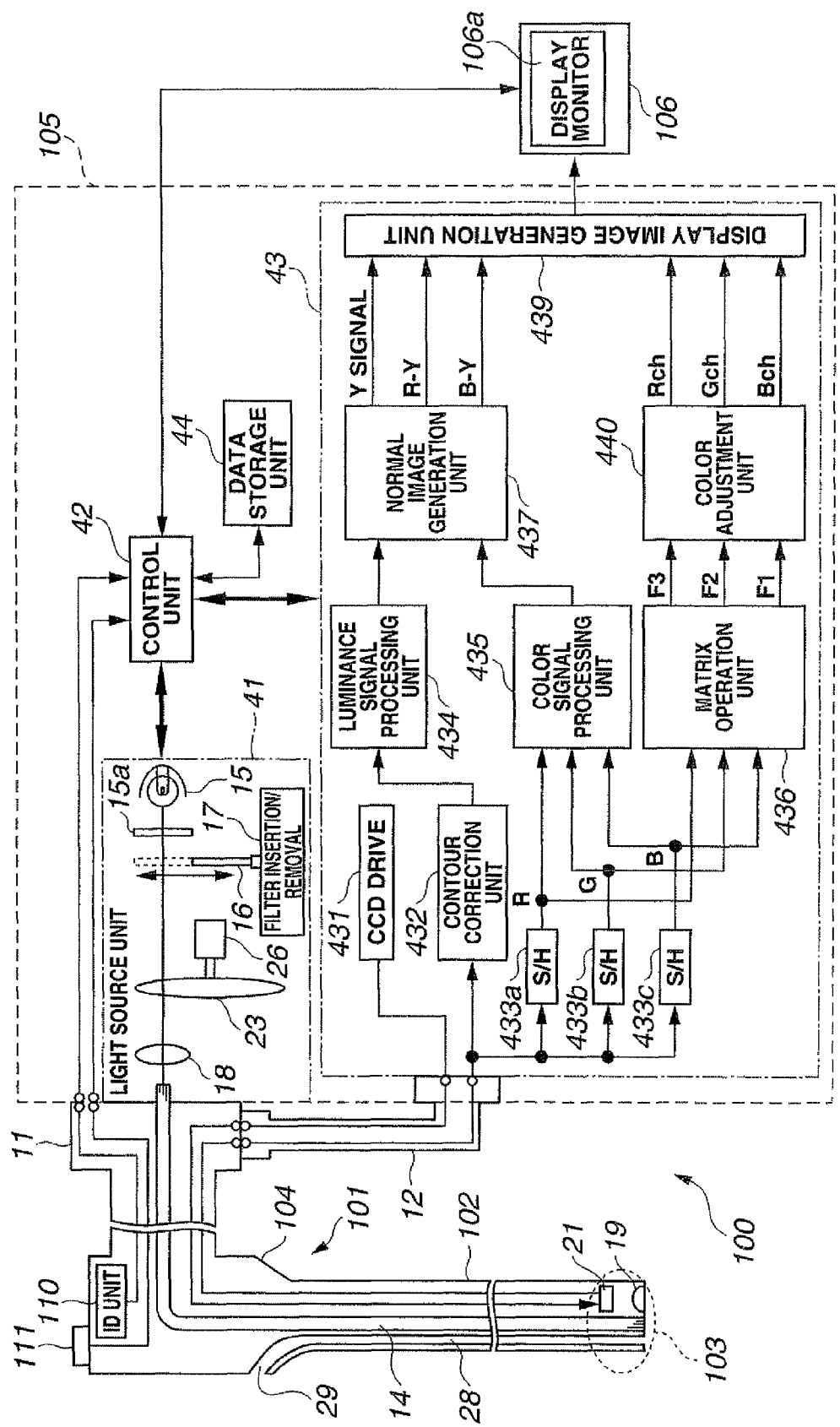
FIG. 37 is a block diagram showing configuration of an electronic endoscope device according to a second embodiment of the present invention.
Figure 38:
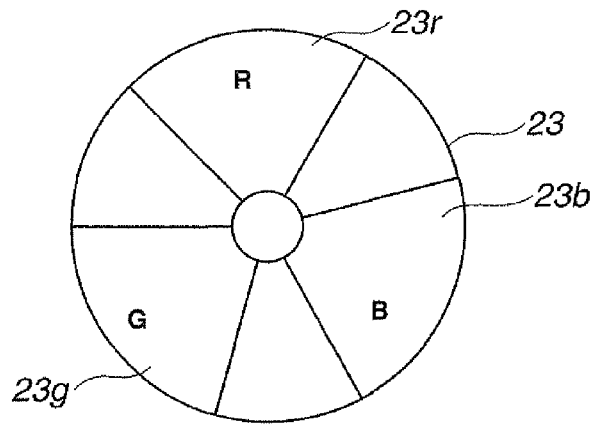
FIG. 38 is a diagram showing configuration of an RGB rotating filter in FIG. 37.
Figure 39:
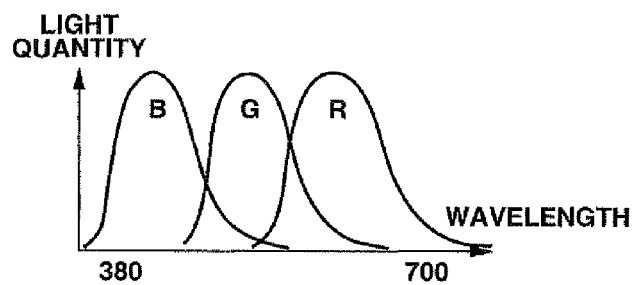
FIG. 39 is a diagram showing spectral characteristics of light that is transmitted through the ROB rotating filter in FIG. 38 when a light quantity limiting filter in a first spectral image generation mode is not on an optical path.
Figure 40:
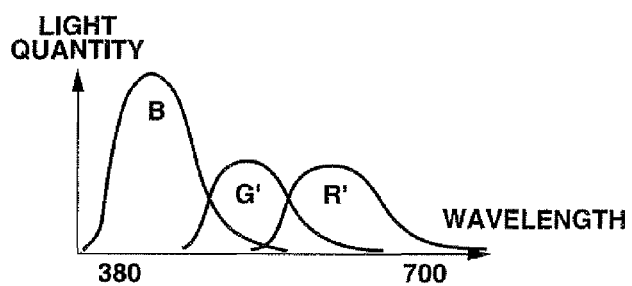
FIG. 40 is a diagram showing spectral characteristics of light that is transmitted through the RGB rotating filter in FIG. 38 when the light quantity limiting filter in a second spectral image generation mode is on an optical path.
Figure 41:
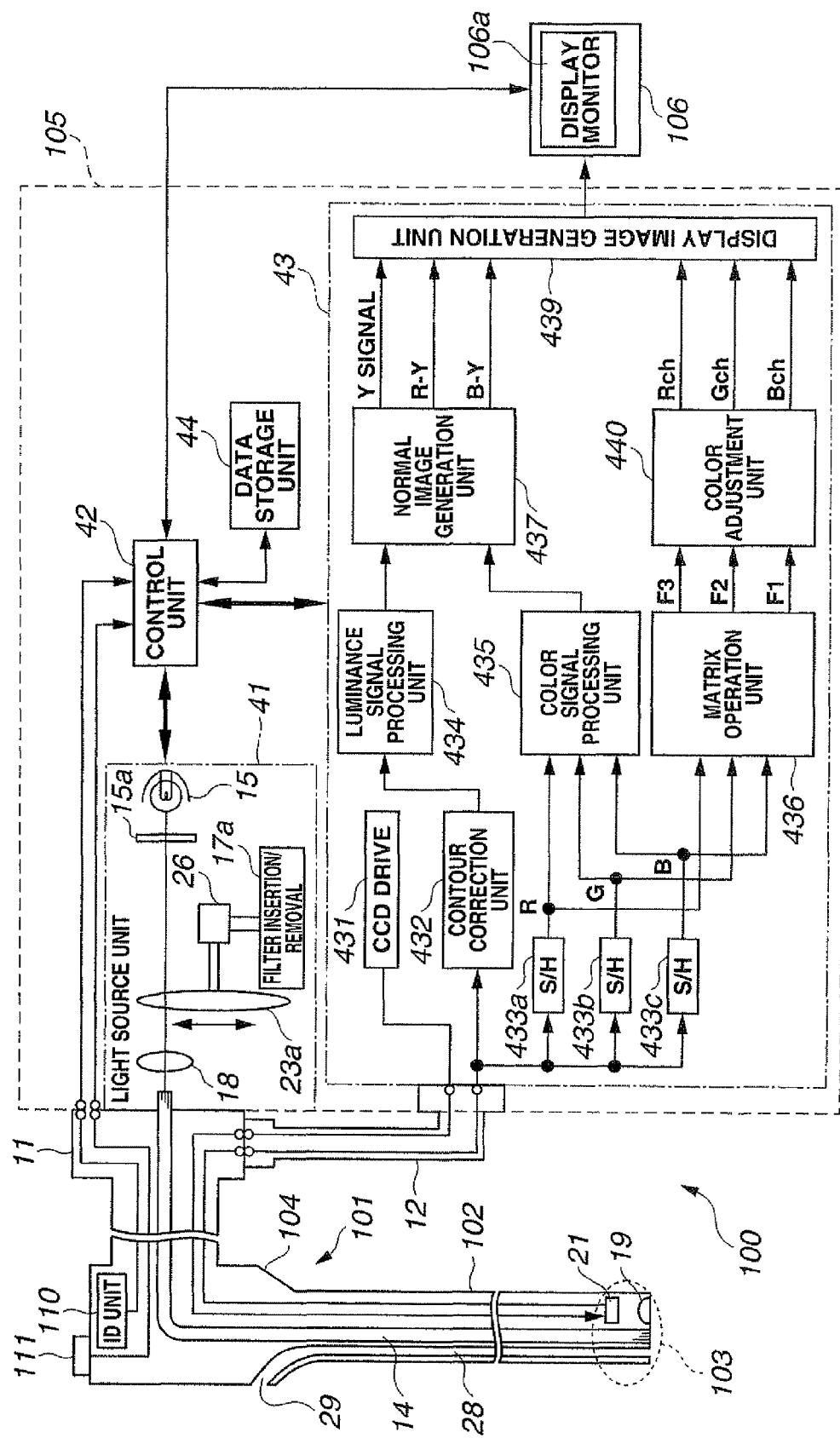
FIG. 41 is a block diagram showing configuration of a variation of the electronic endoscope device in FIG. 37.
Figure 42:
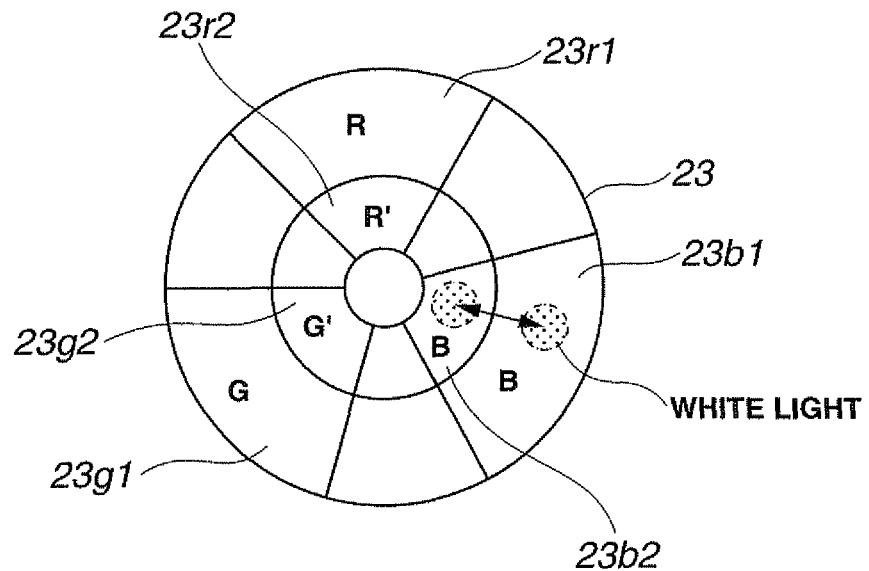
FIG. 42 is a diagram showing configuration of an RGB rotating filter in FIG. 41.
Figure 43:
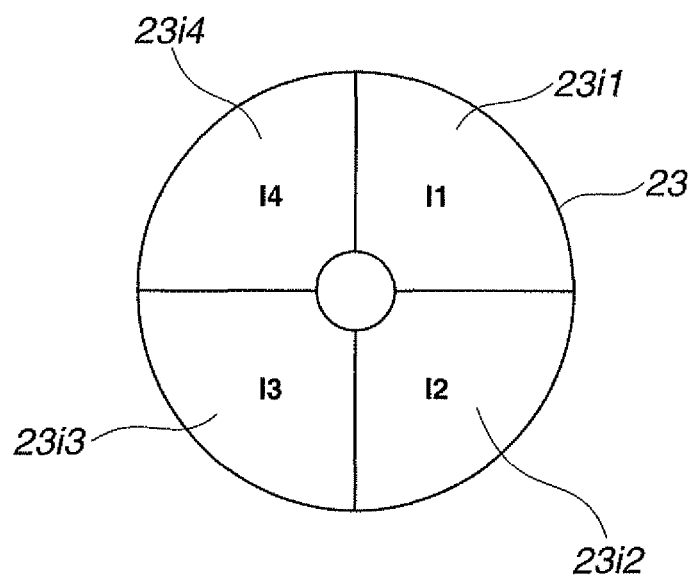
FIG. 43 is a diagram showing configuration of a variation of the RGB rotating filter in FIG. 38.

FIGS. 37 to 43 relate to a second embodiment of the present invention. FIG. 37 is a block diagram showing configuration of an electronic endoscope device; FIG. 38 is a diagram showing configuration of an RGB rotating filter in FIG. 37; FIG. 39 is a diagram showing spectral characteristics of light that is transmitted through the RGB rotating filter in FIG. 38 when a light quantity limiting filter in a first spectral image generation mode is not on an optical path; FIG. 40 is a diagram showing spectral characteristics of light that is transmitted through the RGB rotating filter in FIG. 38 when the light quantity limiting filter in a second spectral image generation mode is on an optical path; FIG. 41 is a block diagram showing configuration of a variation of the electronic endoscope device in FIG. 37; FIG. 42 is a diagram showing configuration of an RGB rotating filter in FIG. 41; and FIG. 43 is a diagram showing configuration of a variation of the RGB rotating filter in FIG. 38.

The second embodiment is almost same as the first embodiment. As such, only different points will be described and the same components are given same numerals and will not be described.

The present embodiment differs from the first embodiment mainly in the light source unit 41 and the CCD 21. According to the first embodiment, the CCD 21 is provided with the color filter shown in FIG. 4, and a so-called simultaneous type is used in which the color filter generates a color signal. On the other hand, according to the present embodiment, so-called frame sequential type is used for illuminating illumination light in an RGB order to generate a color signal.

As shown in FIG. 37, in the light source unit 41 according to the present embodiment, light via the lamp 15, the infrared cut filter 15a and the light quantity limiting filter 16 is transmitted through an RGB filter 23. Similarly to the first embodiment, the light quantity limiting filter 16 is insertably removable on an optical path. The RGB rotating filter 23, which is connected to an RGB rotating filter control unit 26, rotates at a pre-determined rotation speed.

The RGB rotating filter 23 is configured with an R filter unit 23r for transmitting R band light, a G filter unit 23g for transmitting G band light, and a B filter unit 23b for transmitting B band light, as shown in FIG. 38. FIG. 39 shows spectral characteristics of light transmitting the RGB rotating filter 23 in the first spectral image generation mode, i.e., when the light quantity limiting filter 16 is not on an optical path. FIG. 40 shows spectral characteristics of light being transmitted through the RGB rotating filter 23 in the second spectral image generation mode, i.e., when the light quantity limiting filter 16 is on an optical path.

In operation of the light source unit according to the present embodiment, unnecessary infrared components of light flux outputted from the lamp 15 are cut in the infrared cut filter 15a, and light flux being transmitted through the infrared cut filter 15a selectively passes through the light quantity limiting filter 16 and is transmitted through the RGB rotating filter 23, so that the light flux is outputted from the light source unit as R, G and B illumination lights at each pre-determined time. The respective illumination lights reflect in a subject and received by the CCD 21. Signals obtained by the CCD 21 are distributed by a switch unit (not shown) provided for the main body 105 of the endoscope device depending on radiation time, and inputted to the S/H circuits 433a to 433c, respectively. That is, if illumination light is radiated from the light source unit 41 via an R filter, the signals obtained by the CCD 21 are inputted to the S/H circuit 433a. The other operation is similar to the first embodiment and will not be described.

According to the present embodiment, similarly to the first embodiment, by setting a spectral image generation mode to the second spectral image generation mode and transmitting light flux from the lamp 15 through the light quantity limiting filter 16, a spectral image in a blue wavelength band can be improved to image information with similar S/N of spectral images in other wavelength bands, for example.

According to the present embodiment, the light quantity limiting filter 16 is configured to be insertably removable on an optical path, but the embodiment is not limited thereto. Instead, the RGB rotating filter 23 can be configured as shown in FIG. 42 to omit the light quantity limiting filter 16 as shown in FIG. 41.

That is, the rotating filter 23 is configured in a disc shape and has a double structure centering on a rotation axis as shown in FIG. 42. On an outside diameter part of the filter 23, an R filter unit 23r1, the G filter unit 23g1 and the B filter unit 23b1 are arranged that configure a first filter set to output frame sequential light with the spectral characteristics as shown in FIG. 39. On an inside diameter part, an R' filter unit 23r2, a G' filter unit 23g2 and a B filter unit 23b2 are arranged that configure a second filter set to output frame sequential light with the spectral characteristics as shown in FIG. 40.

For the rotating filter 23, the control unit 42 controls driving of a rotating filter motor 26 and rotates the motor 26 as shown in FIG. 41, and the control unit 42 moves the filter 23 in a diameter direction (moves perpendicularly to an optical path of the rotating filter 23, and selectively moves the first filter set or second filter set of the rotating filter 23 on the optical path) through a filter switch motor 17a.

According to the present embodiment, the three R, G and B band frame sequential lights are radiated, but the embodiment is not limited thereto. Instead, the rotating filter 23 can be a rotating filter for transmitting multiband (four or more bands) frame sequential lights 11, 12, 13 and 14 in four different bands as shown in FIG. 43, for example, and for radiating multiband frame sequential lights.

In that case, a spectral image is estimated as in expressions (6) to (8) from four band signals.

[Formula 6]

$$\begin{pmatrix} F1 \\ F2 \\ F3 \end{pmatrix} = K \begin{pmatrix} l1 \\ l2 \\ l3 \\ l4 \end{pmatrix} \quad (6)$$

$$K = \begin{pmatrix} k_1 & k_2 & k_3 & k_4 \\ l_1 & l_2 & l_3 & l_4 \\ m_1 & m_2 & m_3 & m_4 \end{pmatrix}$$

The expression (6) can generate color spectral images with three wavelengths from four band signals.

[Formula 7]

$$F1 = N \begin{pmatrix} l1 \\ l2 \\ l3 \\ l4 \end{pmatrix} \quad (7)$$

$$N = (n_1 \quad n_2 \quad n_3 \quad n_4)$$

The expression (7) can generate a monochrome spectral image with a single wavelength from four band signals.

[Formula 8]

$$\begin{pmatrix} F1 \\ F2 \\ F3 \\ F4 \end{pmatrix} = O \begin{pmatrix} l1 \\ l2 \\ l3 \\ l4 \end{pmatrix} \quad (8)$$

$$O = \begin{pmatrix} o_1 & o_2 & o_3 & o_4 \\ p_1 & p_2 & p_3 & p_4 \\ q_1 & q_2 & q_3 & q_4 \\ r_1 & r_2 & r_3 & r_4 \end{pmatrix}$$

The expression (8) can generate spectral images with four wavelengths from four band signals, and the display image generation unit 439 selects three of the four spectral images to generate a color spectral image.

The above configuration to radiate multiband frame sequential light can estimate spectral images from four band signals, so that the spectral images can be estimated more accurately.

The above configuration to radiate multiband frame sequential lights can realize multiband lights in different bands using a multicolor LED or LD.

The present invention is not limited to the above embodiments. Various changes and alterations can be made without deviating from the scope of the present invention.

What is claimed is:

1. A living body observation device comprising:
   a signal processing control unit for controlling operation of an illumination source for irradiating a living body being a subject with light or an image pickup unit for photoelectrically converting light reflected from the living body based on the illumination light from the illumination source and for generating an image pickup signal, or operations of both the illumination source and the image pickup unit, and for outputting the image pickup signal to a display device;
   a spectral signal generation unit for generating a spectral signal corresponding to a band image of a discrete spectral distribution of said subject from the image pickup signal by signal processing for estimating the spectral signal; and
   a color adjustment unit for adjusting a color tone for each of a plurality of bands forming the spectral signal when the spectral signal is outputted to the display device,
   wherein a spectral characteristics control unit for controlling spectral characteristics of light on an optical path by increasing intensity or sensitivity in a partial wavelength region of the illumination light compared to intensity or sensitivity in other wavelength regions of the illumination light by a spectral intensity control unit for controlling spectral intensity characteristics of the illumination light or an image pickup device spectral sensitivity control unit for controlling spectral sensitivity characteristics of an image pickup device in the image pickup unit is further provided on the optical path from the illumination source to the image pickup unit.

2. The living body observation device according to claim 1, wherein:
   the spectral characteristics control unit increases intensity or sensitivity in a blue wavelength region compared to intensity or sensitivity in other wavelength regions.

3. The living body observation device according to claim 1 including a signal generation control unit for controlling the spectral signal generation unit through a touch-sensitive panel function, wherein:
   the display device includes the touch-sensitive panel function.

4. The living body observation device according to claim 1, wherein the spectral characteristics control unit switches between a mode setting in which the intensity or sensitivity in the partial wavelength region of the illumination light is increased compared to the intensity or sensitivity of the other wavelength regions of the illumination light, and cancellation of the mode setting, in a spectral image generation mode where the spectral image is generated from the spectral signal.

* * * * *